United States Patent
Liao et al.

(10) Patent No.: US 9,193,965 B2
(45) Date of Patent: Nov. 24, 2015

(54) ACETOLACTATE SYNTHASE HAVING 2-KETOISOVALERATE DECARBOXYLASE ACTIVITY AND USES THEREOF

(75) Inventors: James C. Liao, Los Angeles, CA (US); Shota Atsumi, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 264 days.

(21) Appl. No.: 13/095,830

(22) Filed: Apr. 27, 2011

(65) Prior Publication Data
US 2011/0262982 A1 Oct. 27, 2011

Related U.S. Application Data

(60) Provisional application No. 61/328,327, filed on Apr. 27, 2010.

(51) Int. Cl.
| | |
|---|---|
| *C12N 1/20* | (2006.01) |
| *C12N 15/00* | (2006.01) |
| *C12N 9/06* | (2006.01) |
| *C12N 9/16* | (2006.01) |
| *C12P 7/16* | (2006.01) |
| *C07H 21/04* | (2006.01) |
| *C12N 9/88* | (2006.01) |
| *C12N 9/10* | (2006.01) |

(52) U.S. Cl.
CPC ................ *C12N 9/88* (2013.01); *C12N 9/1022* (2013.01); *C12P 7/16* (2013.01); *C12Y 202/01006* (2013.01); *Y02E 50/10* (2013.01)

(58) Field of Classification Search
CPC .... C12N 9/0008; C12N 9/1022; C12N 15/52; C12P 7/16
See application file for complete search history.

(56) References Cited

FOREIGN PATENT DOCUMENTS

WO WO 2008/098227 A2 * 4/2008

OTHER PUBLICATIONS

Atsumi et al. Acetolactate synthase from *Bacillus subtilis* serves as a 2-ketoisovalerate decarboxylase for isobutanol biosynthesis in *Escherichia coli*. Appl Environ Microbiol. Oct. 2009;75(19):6306-11. doi: 10.1128/AEM.01160-09. Epub Aug. 2009.*

Aristidou et al. Modification of central metabolic pathway in *Escherichia coli* to reduce acetate accumulation by heterologous expression of the *Bacillus subtilis* acetolactate synthase gene. Biotechnol Bioeng. Oct. 1994;44(8):944-51.*

Atsumi, S., et al., "Non-Fermentative Pathways for Synthesis of Branched-Chain Higher Alcohols as Biofuels," Nature 451(7174):86-89, Jan. 2008.

Dickinson, J.R., et al., "A $^{13}$C Nuclear Magnetic Resonance Investigation of the Metabolism of Leucine to Isoamyl Alcohol in *Saccharomyces cerevisiae*," Journal of Biological Chemistry 272(43):26871-26878, Oct. 1997.

Gollop, N., et al., "Physiological Implications of the Substrate Specificities of Acetohydroxy Acid Synthases From Varied Organisms," Journal of Bacteriology 172(6):3444-3449, Jun. 1990.

Huseby, N.-E., and F.C. Størmer, "The pH 6 Acetolactate-Forming Enzyme From Aerobacter aerogenes: The Effect of 2-Oxobutyrate Upon the Enzyme Activity," European Journal of Biochemistry 20(2)215-217, May 1971.

Pang, S.S., et al., "The Crystal Structures of *Klebsiella pneumoniae* Acetolactate Synthase With Enzyme-Bound Cofactor and With an Unusual Intermediate," Journal of Biological Chemistry 279(3):2242-2253, Jan. 2004.

* cited by examiner

*Primary Examiner* — Yong Pak
(74) *Attorney, Agent, or Firm* — Christensen O'Connor Johnson Kindness PLLC

(57) ABSTRACT

Provided herein are metabolically-modified microorganisms useful for producing biofuels. More specifically, provided herein are methods of producing high alcohols including isobutanol, 1-butanol, 1-propanol, 2-methyl-1-butanol, 3-methyl-1-butanol, and 2-phenylethanol from a suitable substrate and a recombinant acetolactate synthase having both synthase and decarboxylase activity.

7 Claims, 9 Drawing Sheets

| overexpression | | |
|---|---|---|
| alsS | alsS | alsS |
| ilvC | ilvC | ilvC |
| ilvD | ilvD | ilvD |
| kdc | kdc | ---- |
| adh | ---- | ---- |
| 6.8 ± 0.3 | 7.0 ± 0.5 | 2.7 ± 0.2 |
| isobutanol (g/L/day) | | |

*Fig. 1B.*

ACETOLACTATE SYNTHASE HAVING 2-KETOISOVALERATE DECARBOXYLASE ACTIVITY AND USES THEREOF

CROSS-REFERENCE TO RELATED APPLICATION

This application claims the benefit of U.S. Provisional Application Ser. No. 61/328,327, filed Apr. 27, 2010, the disclosure of which is incorporated herein by reference.

STATEMENT REGARDING SEQUENCE LISTING

The sequence listing associated with this application is provided in text format in lieu of a paper copy and is hereby incorporated by reference into the specification. The name of the text file containing the sequence listing is 36753_SEQ_FINAL.txt. The text file is 64 KB; was created on Apr. 26, 2011; and is being submitted via EFS-Web with the filing of the specification.

TECHNICAL FIELD

The invention relates to polypeptides having 2-ketoisovalerate decarboxylase activity. More particularly, the invention provides recombinant polypeptides having 2-ketoisovalerate activity and biosynthetic pathways having such activity.

BACKGROUND

Artificial or recombinant biosynthetic pathways are useful in the generation of novel byproducts or in the generation of existing products by a new pathway. Enzymes are key players in the production of new byproducts or in modulating biosynthetic pathways.

SUMMARY

The disclosure provides a recombinant microorganism that produces isobutanol wherein the alcohol is produced from a metabolite comprising 2-keto acid and wherein the organism lacks a gene encoding 2-keto acid decarboxylase.

The disclosure also provides a recombinant microorganism that produces isobutanol wherein the alcohol is produced from a metabolite comprising 2-keto acid and wherein the organism expresses a heterologous acetolactate synthase having decarboxylase activity.

The disclosure further provides a recombinant microorganism that produces isobutanol wherein the alcohol is produced from a metabolite comprising 2-keto acid and wherein the organism comprises a heterologous mutant acetolactate synthase lacking 2-keto acid decarboxylase activity and a heterologous 2-keto acid decarboxylase.

In certain embodiments of the foregoing, the microorganism is an *Escherichia coli*. In some embodiments the acetolactate synthase is derived from *Baccilus subtilis*. In yet other embodiments, the microorganism is selected from a genus of *Corynebacterium, Bacillus, Lactobacillus, Lactococcus, Salmonella, Enterobacter, Enterococcus, Erwinia, Pantoea, Morganella, Pectobacterium, Proteus, Serratia, Shigella, Klebsiella, Citrobacter, Saccharomyces, Dekkera, Klyveromyces,* and *Pichia*. In still further embodiments, the biosynthetic pathway for the production of an amino acid in the organism is modified for production of isobutanol. In some embodiments, the microorganism comprises reduced ethanol production capability compared to a parental microorganism.

In certain embodiments, the acetolactate synthase comprises a sequence that is at least 80%, 90%, 95%, 98%, 99% or 100% identical to SEQ ID NO:2 and has acetolactate synthase and decarboxylase activity. In yet other embodiments, the acetolactate synthase comprises a sequence that is at least 80%, 90%, 95%, 98%, or 99% identical to SEQ ID NO:7 and has acetolactate synthase activity and the organism further comprises a 2-keto acid decarboxylase.

The disclosure also provides a method for producing isobutanol, the method comprising culturing a microorganism of the disclosure in the presence of a suitable substrate or metabolic intermediate and under conditions suitable for the conversion of the substrate or metabolic intermediate to isobutanol, and substantially purifying the isobutanol.

The details of one or more embodiments of the disclosure are set forth in the accompanying drawings and the description below. Other features, objects, and advantages will be apparent from the description and drawings, and from the claims.

DESCRIPTION OF THE DRAWINGS

The foregoing aspects and many of the attendant advantages of this invention will become more readily appreciated as the same become better understood by reference to the following detailed description, when taken in conjunction with the accompanying drawings. Like reference symbols in the various drawings indicate like elements.

FIG. 1 shows a schematic representation of the pathway for isobutanol production. FIG. 1B: Isobutanol production with the Kdc-dependent and -independent synthetic pathways. INC, acetohydroxy acid isomeroreductase; IlvD, dihydroxy acid dehydratase.

FIG. 2A: Isobutanol production using various enzymes. FIGS. 2B and 2C: Isobutanol production with the supply of KIV. ND, not detectable.

FIG. 4A: Isobutanol production with the AlsS variants. The cells were grown in M9 medium containing 5 g/liter yeast extract and 36 g/liter glucose in shake flasks at 30° C. with 0.1 mM IPTG for 24 hrs. FIGS. 4B and 4C: Specific growth rate of *E. coli* strain KS145 (ΔilvI 66 ilvB) with the AlsS variants in M9 medium containing 1% glucose and 39.5 µg·ml$^{-1}$ L-isoleucine (FIG. 4B) and 35 µg·ml$^{-1}$ L-valine and 39.5 µg·ml$^{-1}$ L-leucine (FIG. 4C). The ilvC and ilvD genes were over-expressed with the alsS gene.

DETAILED DESCRIPTION

Figure 1A:
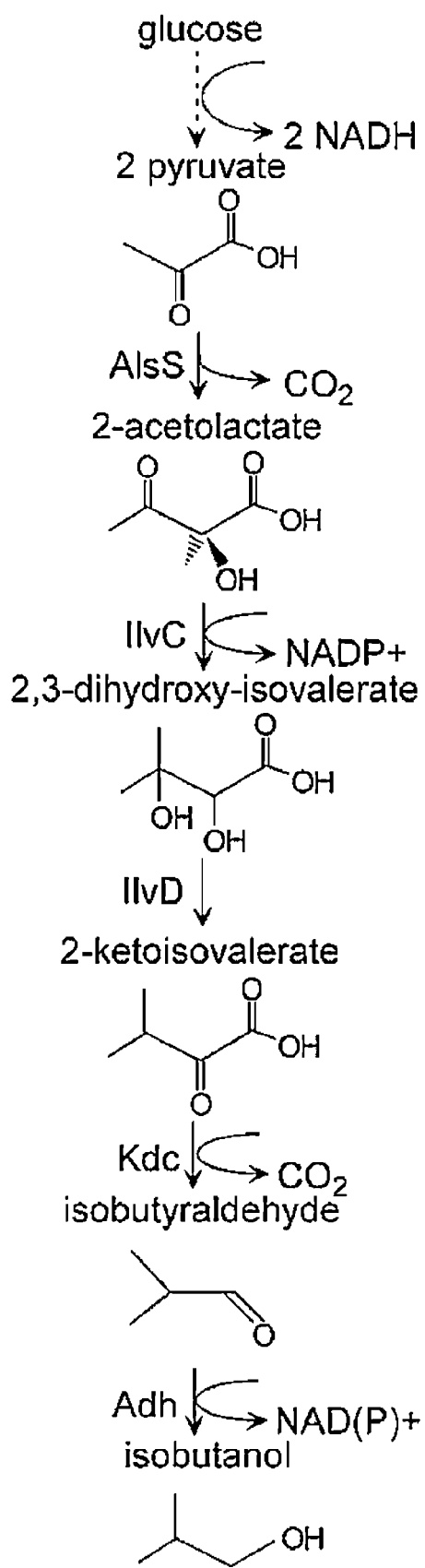
FIG. 1A: The Kdc-dependent synthetic pathway for isobutanol production.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the"

include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Thiamine pyrophosphate (TPP)-dependent enzymes, including 2-keto acid decarboxylase and acetolactate synthase, perform a diverse range of reactions. Acetolactate synthase catalyzes the condensation of two pyruvates to form 2-acetolactate. Isobutanol production from *Escherichia coli* has been demonstrated using a 2-keto acid-based pathway. This pathway contained two TPP-dependent enzymes, acetolactate synthase (ALS) and 2-keto acid decarboxylase (KDC). The present disclosure provides an ALS from *Bacillus subtilis* that catalyzes a decarboxylation of 2-ketoisovalerate like KDC both in vivo and in vitro. The disclosure further provides engineered metabolic pathways comprising such a polypeptide. The disclosure further provides expression of ALS in *E. coli* to produce isobutanol without the presence of KDC. Mutational studies of ALS have revealed that replacement of Q487 with alanine diminishes only decarboxylase activity and maintains synthase activity. The fact that acetolactate synthase catalyzes a decarboxylation reaction supports the hypothesis that TPP-dependent enzymes have diverged from a common ancestor during their evolution.

TPP is a cofactor whose biochemical functions and mechanistic role are well understood. TPP-dependent enzymes perform a diverse range of reactions, including non-oxidative decarboxylation of 2-keto acids, oxidative decarboxylation of 2-keto acids, and carboligation. It is generally accepted that the initial step in catalysis by these enzymes is the deprotonation of the thiazolium ring at the C-2 atom involving a conserved glutamate, N-1', and the 4'-amino group. Protein sequence comparisons of various TPP-dependent enzymes reveal that these enzymes share high sequence homology with each other. In addition, protein structure comparisons of TPP-dependent enzymes: transketolase, pyruvate oxidase, and pyruvate decarboxylase (PDC), indicated that their TPP-binding sites are very similar.

ALS is part of the valine biosynthesis pathway and catalyzes the aldo condensation of two molecules of pyruvate to 2-acetolactate. The overall reaction catalyzed by ALS is irreversible because of $CO_2$ evolution. The first step in catalysis is the ionization of the thiazolium ring of TPP. The highly reactive tricyclic intermediate first forms and this reacts with the first pyruvate that then decarboxylates to give the relatively non-reactive enamine. Because this intermediate is stable, the enzyme can pause midway through the catalytic cycle while releasing $CO_2$ and admitting the second molecule of pyruvate. The tricyclic-carbanion then forms, followed by reacting with the second pyruvate. Deprotonation followed by C—C bond breakage completes the reaction, producing 2-acetolactate.

KDC is a non-oxidative TPP-dependent enzyme. KDCs are rare in bacteria, being more frequent in plants, yeasts, and fungi. A number of KDCs have been identified in various organisms, and these enzymes include PDC, phenylpyruvate decarboxylase, branched-chain 2-keto acid decarboxylase, 2-ketoglutarate decarboxylase, and indole-3-pyruvate decarboxylase. 2-Keto acids are intermediates in amino acid biosynthesis pathways and can be converted to aldehydes by KDCs in the Ehrlich pathway.

In a previous study to produce isobutanol, glucose was converted to 2-ketoisovalerate through over-expressed AlsS (*Bacillus subtilis*), IlvC (*E. coli*), and IlvD (*E. coli*) (FIG. 1) (Atsumi and Liao, Nature, 451:86-89, 2008). The resulting 2-ketoisovalerate (2-KIV) is then converted to isobutanol using Kivd (*Lactoccus lactis*) and Adh2 (*Saccharomyces cerevisiae*) (FIG. 1A). This strain produced 6.8 g/L isobutanol in 24 hrs and more than 20 g/L in 112 hrs (id.).

The present disclosure describes the use of ALS from *B. subtilis* (SEQ ID NO:1 and 2) in a recombinant microorganism for the generation of biofuels including isobutanol. Furthermore, the disclosure provided a variant ALS that can be used in such microorganisms. Both the wild-type and variant ALS can be engineered into a micoroorganism to generate a recombinant metabolic pathway for the generation of a biofuel such as isobutanol in the absence of a KDC.

While these polypeptides and variants will be described in more detail below, it is understood that polypeptides of the disclosure can contain one or more modified amino acids or additional conservative amino acid substitutions. The presence of modified amino acids can be advantageous in, for example, (a) increasing polypeptide in vivo half-life, (b) reducing or increasing polypeptide antigenicity, and (c) increasing polypeptide storage stability. Amino acid(s) are modified, for example, co-translationally or post-translationally during recombinant production (e.g., N-linked glycosylation at N—X—S/T motifs during expression in eukaryotic cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools, or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature.

The polypeptides disclosed herein are useful in the production of biofuels including isobutanol from recombinant microorganisms. In one embodiment, the microorganism is *E. coli*. In another embodiment, the microorganism lacks a gene encoding a 2-keto acid decarboxylase. In yet another embodiment, the microorganism is an *E. coli* that is engineered to express a recombinant ALS or variant thereof and lacks one or more genes encoding enzymes in a competitive metabolic pathway that causes a flux of substrates away from the desired product (e.g., a biofuel such as isobutanol).

The production of isobutanol and other fusel alcohols by various yeast species, including *Saccharomyces cerevisiae*, is of special interest to the distillers of alcoholic beverages, for whom fusel alcohols constitute often undesirable off-notes. Production of isobutanol in wild-type yeasts has been documented on various growth media, ranging from grape must from winemaking (Romano, et al., (2003) *World J. Microbiol. Biotechnol.* 19:311-315), in which 12-219 mg/L isobutanol were produced, to supplemented minimal media (Oliviera, et al. (2005) *World J. Microbiol. Biotechnol.* 21:1569-1576), producing 16-34 mg/L isobutanol. Work from Dickinson, et al., (*J. Biol. Chem.* 272:26871-26878, 1997) has identified the enzymatic steps utilized in a pathway converting branch-chain amino acids (e.g., valine or leucine) to isobutanol.

The present disclosure provides metabolically engineered microorganisms comprising biochemical pathways for the production of higher alcohols including isobutanol from a suitable substrate. A metabolically engineered microorganism of the disclosure comprises one or more recombinant polynucleotides within the genome of the organism or external to the genome within the organism. The microorganism can comprise a reduction, disruption, or knockout of a gene found in the wild-type organism and/or introduction of a heterologous polynucleotide.

The present disclosure also includes metabolically engineered biosynthetic pathways that utilize an organism's native amino acid pathway. Biofuel production utilizing the organism's native amino acid biosynthetic pathways offers several advantages. Not only does it avoid the difficulty of expressing a large set of foreign genes but it also minimizes the possible accumulation of toxic intermediates. Contrary to the butanol production pathway found in many species of *Clostridium*, the engineered amino acid biosynthetic routes for biofuel production circumvent the need to involve oxygen-sensitive enzymes and CoA-dependent intermediates.

In one embodiment, the disclosure provides a recombinant microorganism comprising elevated expression of at least one target enzyme as compared to a parental microorganism or encodes an enzyme not found in the parental organism. In a specific embodiment, the enzyme comprises an acetolactate synthase (ALS). In yet another embodiment, the enzyme comprises an acetolactate synthase from *B. subtilis*. In a further embodiment, the enzyme comprises a sequence as set forth in SEQ ID NO:2 or a variant having at least 80%, 90%, 95%, 98%, or 99% identity to SEQ ID NO:2 and having acetolactate synthase activity. In some embodiments wherein the microorganism comprises an acetolactate synthase from *B. subtilis* or a derivative thereof, the microorganism lacks a 2-keto acid decarboxylase. In a further embodiment, the enzyme comprises a sequence as set forth in SEQ ID NO:7 or a variant having at least 80%, 90%, 95%, 98%, or 99% identity to SEQ ID NO:7, and having acetolactate synthase activity.

In another or further embodiment, the microorganism comprises a reduction, disruption, or knockout of at least one gene encoding an enzyme that competes with a metabolite necessary for the production of a desired higher alcohol product. The recombinant microorganism produces at least one metabolite involved in a biosynthetic pathway for the production of isobutanol or other a higher alcohol. In general, the recombinant microorganism comprises at least one recombinant metabolic pathway that comprises a target enzyme and can further include a reduction in activity or expression of an enzyme in a competitive biosynthetic pathway. The pathway acts to modify a substrate or metabolic intermediate in the production of a biofuel such as isobutanol. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure.

As used herein, the term "metabolically engineered" or "metabolic engineering" involves rational pathway design and assembly of biosynthetic genes, genes associated with operons, and control elements of such polynucleotides, for the production of a desired metabolite, such as a 2-keto acid or a higher alcohol, in a microorganism. "Metabolically engineered" can further include optimization of metabolic flux by regulation and optimization of transcription, translation, protein stability, and protein functionality using genetic engineering and appropriate culture conditions including the reduction of, disruption, or knocking out of, a competing metabolic pathway that competes with an intermediate leading to a desired pathway. A biosynthetic gene can be heterologous to the host microorganism, either by virtue of being foreign to the host, or by being modified by mutagenesis, recombination, and/or association with a heterologous expression control sequence in an endogenous host cell. In one embodiment, where the polynucleotide is xenogenetic to the host organism, the polynucleotide can be codon optimized.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

For example, L-valine is synthesized through a biosynthetic pathway inherent to L-valine which diverges from the intermediate (2-ketoisovalerate) of the L-leucine biosynthesis system. In *Escherichia*, the biosynthesis of L-valine and biosynthesis inherent to L-leucine are carried out by a group of enzymes encoded by ilvGMEDA operon and those encoded by leuABCD operon, respectively.

The ilvGMEDA operon includes ilvG, ilvM, ilvE, ilvD, and ilvA genes. Among them, ilvG encodes acetolactate synthase II large subunit, ilvM encodes acetolactate II synthase small subunit, ilvE encodes branched-chain amino acid amino transferase, ilvD encodes dihydroxyacid dehydratase, and ilvA encodes threonine deaminase. In some species and strains of *E. coli*, ilvG and ilvM are silent.

The leuABCD operon includes leuA, leuB, leuC, and leuD genes. Among them, leuA encodes α-isopropylmalate synthase, leuB encodes β-isopropylmalate dehydrogenase, and leuC and leuD encode α-isopropylmalate isomerase. Of these enzymes, α-isopropylmalate synthase catalyzes the synthetic reaction from α-ketoisovalerate to α-isopropylmalate, α-isopropylmalate isomerase catalyzes the isomerization reaction from α-isopropylmalate to β-isopropylmalate, and β-isopropylmalate dehydrogenase catalyzes the dehydrogenation reaction from β-isopropylmalate to α-ketoisocaproic acid, which is the final intermediate of L-leucine biosynthesis. *Escherichia* possess four kinds of transaminases, namely, transaminase A (aspartate-glutamate aminotransferase) encoded by aspC gene, transaminase B (BCAA aminotransferase) encoded by ilvE gene which is included in ilvGMEDA operon, transaminase C (alanine-valine aminotransferase) encoded by avtA gene and transaminase D (tyrosine aminotransferase) encoded by tyrB gene. These enzymes participate in various amination reactions. Of these enzymes, transaminase B and transaminase D catalyze the abovementioned amination reaction from α-ketoisocaproic acid to L-leucine. Transaminase C and transaminase D catalyze the final step of L-valine biosynthetic pathway, which includes a common pathway among the L-valine biosynthesis and L-leucine biosynthesis pathways.

Expression of ilvBN gene encoding acetohydroxy acid synthase I suffers concerted repression by L-valine and L-leucine, expression of ilvGM gene encoding acetohydroxy acid synthase II suffers concerted repression by L-isoleucine, L-valine, and L-leucine, and expression of ilvIH gene encoding acetohydroxy acid synthase III suffers repression by L-leucine.

The term "substrate" or "suitable substrate" refers to any substance or compound that is converted or meant to be converted into another compound by the action of an enzyme. The term includes not only a single compound, but also combinations of compounds, such as solutions, mixtures, and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein. A "biomass derived sugar" includes, but is not limited to, molecules such as glucose, sucrose, mannose, xylose, and arabinose. The term biomass derived sugar encompasses suitable carbon substrates ordinarily used by microorganisms, such as 6 carbon sugars, including but not limited to glucose, lactose, sorbose, fructose, idose, galactose, and mannose all in either D or L form, or a combination of 6 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA), and D-mannonic acid.

The term "alcohol" includes for example 1-propanol, isobutanol, 1-butanol, 2-methyl-1-butanol, 3-methyl-1-butanol, or 2-phenylethanol. The term "1-butanol" or "n-butanol" generally refers to a straight chain isomer with the alcohol functional group at the terminal carbon. The straight chain isomer with the alcohol at an internal carbon is sec-butanol or 2-butanol. The branched isomer with the alcohol at a terminal carbon is isobutanol, and the branched isomer with the alcohol at the internal carbon is tert-butanol.

Recombinant microorganisms provided herein can express a plurality of target enzymes involved in pathways for the production of, for example, isobutanol, 1-propanol, 1-butanol, 2-methyl-1-butanol, 3-methyl-1-butanol, or 2-phenylethanol using a suitable carbon substrate.

Accordingly, metabolically "engineered" or "modified" microorganisms are produced via the introduction of genetic material into a host or parental microorganism of choice, thereby modifying or altering the cellular physiology and biochemistry of the microorganism. Through the introduction of genetic material, the parental microorganism acquires new properties, e.g., the ability to produce a new, or greater quantities of, an intracellular metabolite. In an illustrative embodiment, the introduction of genetic material into a parental microorganism results in a new or modified ability to produce an alcohol such as isobutanol, 1-propanol, 1-butanol, 2-methyl-1-butanol, 3-methyl-1-butanol, or 2-phenylethanol. The genetic material introduced into the parental microorganism contains gene(s), or parts of genes, coding for one or more of the enzymes involved in a biosynthetic pathway for the production of an alcohol and may also include additional elements for the expression and/or regulation of expression of these genes, e.g., promoter sequences.

An engineered or modified microorganism can also include in the alternative or in addition to the introduction of a genetic material into a host or parental micoorganism, the disruption, deletion, or knocking out of a gene or polynucleotide to alter the cellular physiology and biochemistry of the microorganism. Through the reduction, disruption, or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

The disclosure demonstrates that the expression of one or more heterologous polynucleotide(s) or over-expression of one or more heterologous polynucleotide(s) encoding a polypeptide having both acetolactate synthase and keto acid decarboxylase activity are useful in the generation of isobutanol. In one specific embodiment, the disclosure demonstrates that with over-expression of the heterologous alsS gene from *B. subtilis* and adh2, and the ilvC and IlvD from *E. coli*, the production of isobutanol can be obtained.

Microorganisms provided herein are modified to produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-keto acid), or an end product (e.g., 1-propanol, isobutanol, 1-butanol, 2-methyl-1-butanol, 3-methyl-1-butanol, or 2-phenylethanol) of metabolism.

Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, 1-propanol, isobutanol, 1-butanol, 2-methyl-1-butanol, 3-methyl-1-butanol or 2-phenylethanol, and 2-ketoisovalerate or 2-ketovaleric acids. As depicted in FIG. 1A, exemplary 2-keto acid intermediates include 2-ketobutyrate, 2-ketoisovalerate, 2-ketovalerate, 2-keto 3-methylvalerate, 2-keto 4-methylpentanoate, and phenylpyruvate.

Accordingly, provided herein are recombinant microorganisms that produce isobutanol and in some aspects may include the elevated expression of target enzymes such as acetohydroxy acid synthase (e.g., ilvIH operon, or any other als containing operon), acetohydroxy acid isomeroreductase (e.g., ilvC), dihydroxy-acid dehydratase (e.g., ilvD), and alcohol dehydrogenase (e.g., ADH2). The microorganism can further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, to increase the availability of pyruvate or reduce enzymes that compete for a metabolite in a desired biosynthetic pathway. In some aspects the recombinant microorganism can include the elevated expression of acetolactate synthase (e.g., alsS), acetohydroxy acid isomeroreductase (e.g., ilvC), dihydroxy-acid dehydratase (e.g., ilvD), and alcohol dehydrogenase (e.g., ADH2). With reference to alcohol dehydrogenases, although ethanol dehydrogenase is an alcohol dehydrogenase, the synthesis of ethanol is undesirable as a by-product in the biosynthetic pathways. Accordingly, reference to an increase in alcohol dehydrogenase activity or expression in a microorganism specifically excludes ethanol dehydrogenase activity.

As previously noted the target enzymes described throughout this disclosure generally produce metabolites. For example, the enzymes acetolactate synthase (alsS), acetohydroxy acid isomeroreductase (ilvC), and dihydroxy-acid dehydratase (ilvD) can produce 2-ketoisovalerate from a substrate that includes pyruvate. In addition, the target enzymes described throughout this disclosure are encoded by polynucleotides. For example, acetohydroxy acid isomeroreductase can be encoded by a polynucleotide derived from an ilvC gene. Dihydroxy-acid dehydratase can be encoded by a polynucleotide derived from an ilvD gene. Alcohol dehydrogenase can be encoded by a polynucleotide derived from an ADH2 gene. Additional enzymes and exemplary genes are described throughout this document. Homologs of the various polypeptides and polynucleotides can be derived from any biologic source that provides a suitable polynucleotide encoding a suitable enzyme. Homologs, for example, can be identified by reference to various databases.

The disclosure identifies specific genes useful in the methods, compositions, and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and/or silent mutations. Such modified or mutated polynucleotides and polypeptides can be screened for expression of a functional enzyme activity using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24:216-218). Methodology for optimizing a nucleotide sequence for expression in a plant is provided, for example, in U.S. Pat. No. 6,015,891, and the references cited therein, all incorporated herein in their entirety.

In addition, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural, or genomic analyses to be an enzyme or gene of the second family or species which corresponds to the original enzyme or gene of the first family or species. Most often, homologs will have functional, structural, and/or genomic similarities. Techniques are known to the skilled artisan by which homologs of an enzyme or gene can readily be cloned using genetic probes and PCR. Identity of cloned sequences as a homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.)

As used herein, two proteins (or a region of the proteins) are substantially homologous when the amino acid sequences have at least 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, reference to an als gene includes homologs from other organisms encoding an enzyme having substantially similar enzymatic activity, as well as genes having at least 30, 40, 50, 60, 70, 80, 85, 90, 95, 98, or 99% identity to the referenced gene and which encodes an enzyme having substantially similar enzymatic activity as the referenced gene. In particular, the homologs will have the highest level of amino acid sequence identity in the region of the active site or a co-factor binding site, and any other region of the enzyme necessary for its function.

It is also understood that an isolated nucleic acid molecule encoding a polypeptide homologous to the enzymes described herein can be created by introducing one or more nucleotide substitutions, additions, or deletions into the nucleotide sequence encoding the particular polypeptide, such that one or more amino acid substitutions, additions, or deletions are introduced into the encoded protein. Mutations can be introduced into the polynucleotide by standard techniques, such as site-directed mutagenesis and PCR-mediated mutagenesis. In contrast to those positions where it may be desirable to make non-conservative amino acid substitutions (see above), in some positions it is preferable to make conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In addition, the following five groups each contain amino acids that are conservative substitutions for one another: 1) Serine (S), Threonine (T); 2) Asparagine (N), Glutamine (Q); 3) Arginine (R), Lysine (K); 4) Isoleucine (I), Leucine (L), Methionine (M), Alanine (A), Valine (V), and 5) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions, and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used for comparing a molecule sequence to a database containing a large number of sequences from different organisms is the computer program BLAST (Altschul, *J. Mol. Biol.* 215:403-441 (1990); Gish, *Nature Genet.* 3:266-272 (1993); Madden, *Meth. Enzymol.* 266:131-141 (1996); Altschul, *Nucl. Acids Res.* 25:3389-3402 (1997); Zhang, *Genome Res.* 7:649-656 (1997)), especially blastp or tblastn (Altschul, *Nucl. Acids Res.* 25:3389-3402 (1997)). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers for various genes, homologs and variants useful in the generation of recombinant microorganisms described herein. It is to be understood that homologs and variants described herein are exemplary and non-limiting. Additional homologs, variants and sequences are available to those of skill in the art using various databases including, for example, the National Center for Biotechnology Information (NCBI), access to which is available on the World-Wide-Web.

Ethanol Dehydrogenase (also referred to as Aldehyde-alcohol DeHydrogenase) is encoded in *E. coli* by adhE. adhE comprises three activities: alcohol dehydrogenase (ADH); acetaldehyde/acetyl-CoA dehydrogenase (ACDH); pyruvate-formate-lyase deactivase (PFL deactivase); PFL deactivase activity catalyzes the quenching of the pyruvate-formate-lyase catalyst in an iron, NAD, and CoA dependent reaction. A decrease or modification of the expression or activity of ethanol dehydrogenase in a transformed host cell can be useful in the presently disclosed methods for the production of an alcohol, such as isobutanol, 2-methyl 1-butanol, and/or 2-methyl 1-butanol. Homologs are known in the art (see, e.g., aldehyde-alcohol dehydrogenase (*Polytomella* sp. Pringsheim 198.80) gi|40644910|emb|CAD42653.2| (40644910); aldehyde-alcohol dehydrogenase (*Clostridium botulinum* A str. ATCC 3502) gi|148378348|ref|YP_001252889.1|(148378348); aldehyde-alcohol dehydrogenase (*Yersinia pestis* CO92) gi|16122410|ref|NP_405723.1| (16122410); aldehyde-alcohol dehydrogenase (*Yersinia pseudotuberculosis* IP 32953) gi|51596429|ref|YP_070620.1|(51596429); aldehyde-alcohol dehydrogenase (*Yersinia pestis* CO92) gi|115347889|emb|CAL20810.1| (115347889); aldehyde-alcohol dehydrogenase (*Yersinia pseudotuberculosis* IP 32953) gi|5158971|emb|CAH21341.1|(51589711); aldehyde-alcohol dehydrogenase (*Escherichia coli* CFT073) gi|26107972|gb|AAN80172.1|AE016760_31(26107972); aldehyde-alcohol dehydrogenase (*Yersinia pestis* biovar Microtus str. 91001) gi|45441777|ref|NP_993316.1| (45441777); aldehyde-alcohol dehydrogenase (*Yersinia pestis* biovar Microtus str. 91001) gi|45436639|gb|AAS62193.1| (45436639); aldehyde-alcohol dehydrogenase (*Clostridium perfringens* ATCC 13124) gi|110798574|ref|YP_697219.1| (110798574); aldehyde-alcohol dehydrogenase (*Shewanella oneidensis* MR-1) gi|24373696|ref|NP_717739.1| (24373696); aldehyde-alcohol dehydrogenase (*Clostridium botulinum* A str. ATCC 19397) gi|153932445|ref|YP_001382747.1|(153932445); aldehyde-alcohol dehydrogenase (*Yersinia pestis* biovar Antigua str. E1979001) gi|165991833|gb|EDR44134.1|(165991833); aldehyde-alcohol dehydrogenase (*Clostridium botulinum* A str. Hall) gi|153937530|ref|YP_001386298.1|(153937530); aldehyde-alcohol dehydrogenase (*Clostridium perfringens* ATCC 13124) gi|110673221|gb|ABG82208.1|(110673221); aldehyde-alcohol dehydrogenase (*Clostridium botulinum* A str. Hall) gi|15293344|gb|ABS38943.1|(152933444); aldehyde-alcohol dehydrogenase (*Yersinia pestis* biovar Orientalis str. F1991016) gi|165920640|gb|EDR37888.1| (165920640); aldehyde-alcohol dehydrogenase (*Yersinia pestis* biovar Orientalis str. IP275) gi|165913933|gb|EDR32551.1|(165913933); aldehyde-alcohol dehydrogenase (*Yersinia pestis* Angola) gi|162419116|ref|YP_001606617.1|(162419116); aldehyde-alcohol dehydrogenase (*Clostridium botulinum* F str. Langeland) gi|153940830|ref|YP_001389712.1| (153940830); aldehyde-alcohol dehydrogenase (*Escherichia coli* HS) gi|157160746|ref|YP_001458064.1|(157160746); aldehyde-alcohol dehydrogenase (*Escherichia coli* E24377A) gi|157155679|ref|YP_001462491.1| (157155679); aldehyde-alcohol dehydrogenase (*Yersinia enterocolitica* subsp. *enterocolitica* 8081) gi|123442494|ref|YP_001006472.1|(123442494); aldehyde-alcohol dehydrogenase (*Synechococcus* sp. JA-3-3Ab) gi|86605191|ref|YP_473954.1|(86605191); aldehyde-alcohol dehydrogenase (*Listeria monocytogenes* str. 4b F2365) gi|46907864|ref|YP_014253.1|(46907864); aldehyde-alcohol dehydrogenase (*Enterococcus faecalis* V583) gi|29375484|ref|NP_814638.1|(29375484); aldehyde-alcohol dehydrogenase (*Streptococcus agalactiae* 2603V/R) gi|22536238|ref|NP_687089.1|(22536238); aldehyde-alcohol dehydrogenase (*Clostridium botulinum* A str. ATCC 19397) gi|152928489|gb|ABS33989.1|(152928489); aldehyde-alcohol dehydrogenase (*Escherichia coli* E24377A) gi|157077709|gb|ABV17417.1|(157077709); aldehyde-alcohol dehydrogenase (*Escherichia coli* HS) gi|157066426|gb|AB V05681.1|(157066426); aldehyde-alcohol dehydrogenase (*Clostridium botulinum* F str. Langeland) gi|152936726|gb|ABS42224.1|(152936726); aldehyde-alcohol dehydrogenase (*Yersinia pestis* CA88-4125) gi|149292312|gb|EDM42386.1|(149292312); aldehyde-alcohol dehydrogenase (*Yersinia enterocolitica* subsp. *enterocolitica* 8081) gi|122089455|emb|CAL12303.1| (122089455); aldehyde-alcohol dehydrogenase (*Chlamydomonas reinhardtii*) gi|92084840|emb|CAF04128.1|(92084840); aldehyde-alcohol dehydrogenase (*Synechococcus* sp. JA-3-3Ab) gi|86553733|gb|ABC98691.1|(86553733); aldehyde-alcohol dehydrogenase (*Shewanella oneidensis* MR-1) gi|24348056|gb|AAN55183.1|AE015655_9 (24348056); aldehyde-alcohol dehydrogenase (*Enterococcus faecalis* V583) gi|29342944|gb|AAO80708.1|(29342944); aldehyde-alcohol dehydrogenase (*Listeria monocytogenes* str. 4b F2365) gi|46881133|gb|AAT04430.1|(46881133); aldehyde-alcohol dehydrogenase (*Listeria monocytogenes* str. 1/2a F6854) gi|47097587|ref|ZP_00235115.1|(47097587); aldehyde-alcohol dehydrogenase (*Listeria monocytogenes* str. 4b H7858) gi|47094265|ref|ZP_00231973.1| (47094265); aldehyde-alcohol dehydrogenase (*Listeria monocytogenes* str. 4b H7858) gi|47017355|gb|EAL08180.1|(47017355); aldehyde-alcohol dehydrogenase (*Listeria monocytogenes* str. 1/2a F6854) gi|47014034|gb|EAL05039.1|(47014034); aldehyde-alcohol dehydrogenase (*Streptococcus agalactiae* 2603V/R) gi|22533058|gb|AAM98961.11AE014194_6(22533058)$_p$; aldehyde-alcohol dehydrogenase (*Yersinia pestis* biovar Antigua str. E1979001) gi|166009278|ref|ZP_02230176.1| (166009278); aldehyde-alcohol dehydrogenase (*Yersinia pestis* biovar Orientalis str. IP275) gi|165938272|ref|ZP_02226831.1|(165938272); aldehyde-alcohol dehydrogenase (*Yersinia pestis* biovar Orientalis str. F1991016) gi|165927374|ref|ZP_02223206.1|(165927374); aldehyde-alcohol dehydrogenase (*Yersinia pestis* Angola) gi|162351931|gb|ABX85879.1|(162351931); aldehyde-alcohol dehydrogenase (*Yersinia pseudotuberculosis* IP 31758) gi|153949366|ref|YP_001400938.1|(153949366); aldehyde-alcohol dehydrogenase (*Yersinia pseudotuberculosis* IP 31758) gi|152960861|gb|ABS48322.1|(152960861); aldehyde-alcohol dehydrogenase (*Yersinia pestis* CA88-4125) gi|149365899|ref|ZP_01887934.1|(149365899); acetaldehyde dehydrogenase (acetylating) (*Escherichia coli* CFT073) gi|26247570|ref|NP_753610.1|(26247570); aldehyde-alcohol dehydrogenase (includes: alcohol dehydrogenase; acetaldehyde dehydrogenase (acetylating) (EC 1.2.1.10) (acdh); pyruvate-formate-lyase deactivase (pfl deactivase)) (*Clostridium botulinum* A str. ATCC 3502) gi|148287832|emb|CAL81898.1|(148287832); aldehyde-alcohol dehydrogenase (Includes: alcohol dehydrogenase (ADH); acetaldehyde dehydrogenase (acetylating) (ACDH); pyruvate-formate-lyase deactivase (PFL deactivase)) gi|71152980|sp|P0A9Q7.2|ADHE_ECOLI(71152980); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCRI1043) gi|50121254|ref|YP_050421.1| (50121254); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCRI1043) gi|49611780|emb|CAG75229.1|(49611780); aldehyde-alcohol dehydrogenase (includes: alcohol dehydrogenase (ADH); acetaldehyde dehydrogenase (acetylating) (ACDH)) gi|19858620|sp|P33744.3|ADHE_CLOAB (19858620); aldehyde-alcohol dehydrogenase (includes: alcohol dehydrogenase (ADH); acetaldehyde dehydrogenase (acetylating) (ACDH); pyruvate-formate-lyase deactivase (PFL deactivase)) gi|71152683|sp|P0A9Q8.2|ADHE_ECO57 (71152683); aldehyde-alcohol dehydrogenase (includes: alcohol dehydrogenase; acetaldehyde dehydrogenase (acetylating); pyruvate-formate-lyase deactivase (*Clostridium difficile* 630) gi|126697906|ref|YP_001086803.1| (126697906); aldehyde-alcohol dehydrogenase (includes: alcohol dehydrogenase; acetaldehyde dehydrogenase (acetylating); pyruvate-formate-lyase deactivase (*Clostridium difficile* 630) gi|115249343|emb|CAJ67156.1|(115249343); aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|37526388|ref|NP_929732.1|(37526388); aldehyde-alcohol dehydrogenase 2 (includes: alcohol dehydrogenase; acetaldehyde dehydrogenase) (*Streptococcus pyogenes* str. Manfredo) gi|134271169|emb|CAM29381.1|(134271169); aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (Photorhabdus luminescens subsp. *laumondii* TTO1) gi|36785819|emb|CAE14870.1|(36785819); aldehyde-alcohol dehydrogenase (includes: alcohol dehydrogenase and pyruvate-formate-lyase deactivase (*Clostridium difficile* 630) gi|126700586|ref|YP_001089483.1|(126700586); aldehyde-alcohol dehydrogenase (includes: alcohol dehydrogenase and pyruvate-formate-lyase deactivase (*Clostridium difficile* 630) gi|115252023|emb|CAJ69859.1|(115252023); aldehyde-alcohol dehydrogenase 2 (*Streptococcus pyogenes* str. Manfredo) gi|139472923|ref|YP_001127638.1| (139472923); aldehyde-alcohol dehydrogenase E (*Clostridium perfringens* str. 13) gi|18311513|ref|NP_563447.1|(18311513); aldehyde-alcohol dehydrogenase E (*Clostridium perfringens* str. 13) gi|18146197|dbj|BAB82237.1|(18146197); aldehyde-alcohol dehydrogenase, ADHE1 (*Clostridium acetobutylicum* ATCC 824) gi|15004739|ref|NP_149199.1|(15004739); aldehyde-alcohol dehydrogenase, ADHE1 (*Clostridium acetobutylicum* ATCC 824) gi|14994351|gb|AAK76781.1|AE001438_34(14994351); aldehyde-alcohol dehydrogenase 2 (includes: alcohol dehydrogenase (ADH); acetaldehyde/acetyl-CoA dehydrogenase (ACDH)) gi|2492737|sp|Q24803.1|ADH2-ENTHI (2492737); alcohol dehydrogenase (*Salmonella enterica* subsp. *enterica* serovar Typhi str. CT18) gi|16760134|ref|NP_455751.1|(16760134); and alcohol dehydrogenase (*Salmonella enterica* subsp. *enterica* serovar Typhi) gi|16502428|emb|CAD08384.1|(16502428)), each sequence associated with the accession number is incorporated herein by reference in its entirety.

Lactate Dehydrogenase (also referred to as D-lactate dehydrogenase and fermentive dehydrogenase) is encoded in *E. coli* by ldhA and catalyzes the NADH-dependent conversion of pyruvate to D-lactate. A decrease or modification of the expression or activity of LdhA in a transformed host cell can be useful in the presently disclosed methods for the production of an alcohol, such as for example, isobutanol, 2-methyl 1-butanol, or 3-methyl 1-butanol. LdhA homologs and variants are known. In fact there are currently 1664 bacterial lactate dehydrogenases available through NCBI. Homologs and variants include, for example, D-lactate dehydrogenase (D-LDH) (fermentative lactate dehydrogenase) gi|1730102|sp|P52643.1|LDHD_ECOLI(1730102); D-lactate dehydrogenase gi|1049265|gb|AAB51772.1|(1049265); D-lactate dehydrogenase (*Escherichia coli* APEC O1) gi|117623655|ref|YP_852568.1|(117623655); D-lactate dehydrogenase (*Escherichia coli* CFT073) gi|26247689|ref|NP_753729.1|(26247689); D-lactate dehydrogenase (*Escherichia coli* O157:H7 EDL933) gi|15801748|ref|NP_287766.1|(15801748); D-lactate dehydrogenase (*Escherichia coli* APEC O1) gi|115512779|gb|ABJ00854.1|(115512779); D-lactate dehydrogenase (*Escherichia coli* CFT073) gi|26108091|gb|AAN80291.1|AE016760_150 (26108091); fermentative D-lactate dehydrogenase, NAD-dependent (*Escherichia coli* K12) gi|16129341|ref|NP_415898.1|(16129341); fermentative D-lactate dehydrogenase, NAD-dependent (*Escherichia coli* UTI89) gi|91210646|ref|YP_540632.1|(91210646); fermentative D-lactate dehydrogenase, NAD-dependent (*Escherichia coli* K12) gi|1787645|gb|AAC74462.1|(1787645); fermentative D-lactate dehydrogenase, NAD-dependent (*Escherichia coli* W3110) gi|89108227|ref|AP_002007.1|(89108227); fermentative D-lactate dehydrogenase, NAD-dependent (*Escherichia coli* W3110) gi|1742259|dbj|BAA14990.1| (1742259); fermentative D-lactate dehydrogenase, NAD-dependent (*Escherichia coli* UTI89) gi|91072220|gb|ABE07101.1|(91072220); fermentative D-lactate dehydrogenase, NAD-dependent (*Escherichia coli* O157:H7 EDL933) gi|12515320|gb|AAG56380.1|AE005366_6(12515320); fermentative D-lactate dehydrogenase (*Escherichia coli* O157:H7 str. Sakai) gi|13361468|dbj|BAB35425.1| (13361468); COG1052: Lactate dehydrogenase and related dehydrogenases (*Escherichia coli* 101-1) gi|83588593|ref|ZP_00927217.1|(83588593); COG1052: Lactate dehydrogenase and related dehydrogenases (*Escherichia coli* 53638) gi|75515985|ref|ZP_00738103.1| (75515985); COG1052: lactate dehydrogenase and related dehydrogenases (*Escherichia coli* E22) gi|75260157|ref|ZP_00731425.1|(75260157); COG1052: lactate dehydrogenase and related dehydrogenases (*Escherichia coli* F11) gi|75242656|ref|ZP_00726400.1| (75242656); COG1052: lactate dehydrogenase and related dehydrogenases (*Escherichia coli* E110019) gi|75237491|ref|ZP_00721524.1|(75237491); COG1052: lactate dehydrogenase and related dehydrogenases (*Escherichia coli* B7A) gi|75231601|ref|ZP_00717959.1| (75231601); and COG1052: lactate dehydrogenase and related dehydrogenases (*Escherichia coli* B171) gi|75211308|ref|ZP_00711407.1|(75211308), each sequence associated with the accession number is incorporated herein by reference in its entirety.

Two membrane-bound, FAD-containing enzymes are responsible for the catalysis of fumarate and succinate interconversion; the fumarate reductase is used in anaerobic growth, and the succinate dehydrogenase is used in aerobic growth. Fumarate reductase comprises multiple subunits (e.g., frdA, B, and C in *E. coli*). Modification of any one of the subunits can result in the desired activity herein. For example, a knockout of frdB, frdC or frdBC is useful in the methods of the disclosure. Frd homologs and variants are known. Homologs and variants includes, for example, fumarate reductase subunit D (fumarate reductase 13 kDa hydrophobic protein) gi|67463543|sp|P0A8Q3.1|FRDD_ECOLI (67463543); fumarate reductase subunit C (fumarate reductase 15 kDa hydrophobic protein) gi|1346037|sp|P20923.2|FRDC_PROVU(1346037); fumarate reductase subunit D (fumarate reductase 13 kDa hydrophobic protein) gi|120499|sp|P20924.1|FRDD_PROVU (120499); fumarate reductase subunit C (fumarate reductase 15 kDa hydrophobic protein) gi|67463538|sp|P0A8Q0.1|FRDC_ECOLI(67463538); fumarate reductase iron-sulfur subunit (*Escherichia coli*) gi|145264|gb|AAA23438.1|(145264); fumarate reductase flavoprotein subunit (*Escherichia coli*) gi|145263|gb|AAA23437.1|(145263); fumarate reductase flavoprotein subunit gi|37538290|sp|P17412.3|FRDA_WOLSU(37538290); fumarate reductase flavoprotein subunit gi|120489|sp|P00363.3|FRDA_ECOLI(120489); fumarate reductase flavoprotein subunit gi|120490|sp|P20922.1|FRDA_PROVU(120490); Fumarate reductase flavoprotein subunit precursor (flavocytochrome c)

(flavocytochrome c3) (Fcc3) gi|119370087|sp|Q07WU7.2|FRDA_SHEFN(119370087); fumarate reductase iron-sulfur subunit gi|81175308|sp|P0AC47.2|FRDB_ECOLI(81175308); fumarate reductase flavoprotein subunit (flavocytochrome c) (flavocytochrome c3) (Fcc3) gi|119370088|sp|P0C278.1|FRDA_SHEFR(119370088); frd operon uncharacterized protein C gi|140663|sp|P20927.1|YFRC_PROVU(140663); frd operon probable iron-sulfur subunit A gi|140661|sp|P20925.1|YFRA_PROVU(140661); fumarate reductase iron-sulfur subunit gi|120493|sp|P20921.2|FRDB_PROVU(120493); fumarate reductase flavoprotein subunit gi|2494617|sp|O06913.2|FRDA_HELPY(2494617); fumarate reductase flavoprotein subunit precursor (Iron(III)-induced flavocytochrome C3) (Ifc3) gi|13878499|sp|Q9Z4P0.1|FRD2-SHEFN(13878499); fumarate reductase flavoprotein subunit gi|54041009|sp|P64174.1|FRDA-MYCTU(54041009); fumarate reductase flavoprotein subunit gi|54037132|sp|P64175.1|FRDA_MYCBO(54037132); fumarate reductase flavoprotein subunit gi|12230114|sp|Q9ZMP0.1|FRDA_HELPJ(12230114); fumarate reductase flavoprotein subunit gi|1169737|sp|P44894.1|FRDA_HAEIN(1169737); fumarate reductase flavoprotein subunit (Wolinella succinogenes) gi|13160058|emb|CAA04214.21(13160058); fumarate reductase flavoprotein subunit precursor (favocytochrome c) (FL cyt) gi|25452947|sp|P83223.2|FRDA_SHEON (25452947); fumarate reductase iron-sulfur subunit (Wolinella succinogenes) gi|2282000|emb|CAA04215.1| (2282000); and fumarate reductase cytochrome b subunit (Wolinella succinogenes) gi|2281998|emb|CAA04213.1| (2281998), each sequence associated with the accession number is incorporated herein by reference in its entirety.

Acetate kinase is encoded in *E. coli* by ackA. AckA is involved in conversion of acetyl-coA to acetate. Specifically, ackA catalyzes the conversion of acetyl-phosphate to acetate. A decrease or modification of the expression or activity of AckA in a transformed host cell can be useful in the presently disclosed methods for the production of isobutanol. AckA homologs and variants are known. The NCBI database list includes approximately 1450 polypeptides as bacterial acetate kinases. For example, such homologs and variants include acetate kinase (*Streptomyces coelicolor* A3(2)) gi|21223784|ref|NP_629563.1|(21223784); acetate kinase (*Streptomyces coelicolor* A3(2)) gi|6808417|emb|CAB70654.1|(6808417); acetate kinase (*Streptococcus pyogenes* M1 GAS) gi|15674332|ref|NP_268506.1|(15674332); acetate kinase (*Campylobacter jejuni* subsp. *jejuni* NCTC 11168) gi|15792038|ref|NP_281861.1| (15792038); acetate kinase (*Streptococcus pyogenes* M1 GAS) gi|13621416|gb|AAK33227.1|(13621416); acetate kinase (*Rhodopirellula baltica* SH 1) gi|32476009|ref|NP_869003.1|(32476009); acetate kinase (*Rhodopirellula baltica* SH 1) gi|32472045|ref|NP_865039.1|(32472045); acetate kinase (*Campylobacter jejuni* subsp. *jejuni* NCTC 11168) gi|112360034|emb|CAL34826.11 (112360034); acetate kinase (*Rhodopirellula baltica* SH 1) gi|32446553|emb|CAD76388.11 (32446553); acetate kinase (*Rhodopirellula baltica* SH 1) gi|32397417|emb|CAD72723.11 (32397417); AckA (*Clostridium kluyveri* DSM 555) gi|153954016|ref|YP_001394781.11 (153954016); acetate kinase (*Bifidobacterium longum* NCC2705) gi|23465540|ref|NP_696143.1| (23465540); AckA (*Clostridium kluyveri* DSM 555) gi|146346897|gb|EDK33433.1|(146346897); acetate kinase (*Corynebacterium diphtheriae*) gi|38200875|emb|CAE50580.1|(38200875); acetate kinase (*Bifidobacterium longum* NCC2705) gi|233262031 gb|AAN24779.1|(23326203); acetate kinase (Acetokinase) gi|67462089|sp|P0A6A3.1|ACKA_ECOLI(67462089); and AckA (*Bacillus licheniformis* DSM 13) gi|52349315|gb|AAU41949.1|(52349315), the sequences associated with such accession numbers are incorporated herein by reference.

Phosphate acetyltransferase (PTA) is encoded in *E. coli* by the gene designated pta. PTA is involved in conversion of acetate to acetyl-CoA. Specifically, PTA catalyzes the conversion of acetyl-coA to acetyl-phosphate. A decrease or modification of the expression or activity of PTA in a transformed host cell can be useful in the presently disclosed methods for the production of isobutanol. PTA homologs and variants are known. There are approximately 1075 bacterial phosphate acetyltransferases available on NCBI. For example, such homologs and variants include phosphate acetyltransferase Pta (*Rickettsia felis* URRWXCa12) gi|67004021|gb|AAY60947.1|(67004021); phosphate acetyltransferase (*Buchnera aphidicola* str. Cc (*Cinara cedri*)) gi|116256910|gb|ABJ90592.1|(116256910); pta (*Buchnera aphidicola* str. Cc (*Cinara cedri*)) gi|116515056|ref|YP_802685.1|(116515056); pta (*Wigglesworthia glossinidia* endosymbiont of *Glossina brevipalpis*) gi|25166135|dbj|BAC24326.1|(25166135); Pta (*Pasteurella multocida* subsp. *multocida* str. Pm70) gi|12720993| gb|AAK02789.1|(12720993); Pta (*Rhodospirillum rubrum*) gi|25989720|gb|AAN75024.1| (25989720); pta (*Listeria welshimeri* serovar 6b str. SLCC5334) gi|116742418|emb|CAK21542.1|(116742418); Pta (*Mycobacterium avium* subsp. *paratuberculosis* K-10) gi|41398816|gb|AAS06435.1|(41398816); phosphate acetyltransferase (pta) (*Borrelia burgdorferi* B31) gi|15594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|15741311 gb|AAC22857.1|(1574131); phosphate acetyltransferase (Pta) (*Rickettsia bellii* RML369-C) gi|91206026|ref|YP_538381.1|(91206026); phosphate acetyltransferase (Pta) (*Rickettsia bellii* RML369-C) gi|91206025|ref|YP_538380.1|(91206025); phosphate acetyltransferase (pta) (*Mycobacterium tuberculosis* F11) gi|148720131|gb|ABR04756.1|(148720131); phosphate acetyltransferase (pta) (*Mycobacterium tuberculosis* str. Haarlem) gi|1341488861 gb|EBA40931.1|(134148886); phosphate acetyltransferase pta (*Mycobacterium tuberculosis* C) gi|124599819|gb|EAY58829.1|(124599819); phosphate acetyltransferase (Pta) (*Rickettsia bellii* RML369-C) gi|91069570|gb|ABE05292.1|(91069570); phosphate acetyltransferase Pta (*Rickettsia bellii* RML369-C) gi|91069569|gb|ABE05291.1|(91069569); phosphate acetyltransferase (pta) (*Treponema pallidum* subsp. *pallidum* str. Nichols) gi|15639088|ref|NP_218534.1|(15639088); and phosphate acetyltransferase (pta) (*Treponema pallidum* subsp. *pallidum* str. Nichols) gi|3322356|gb|AAC65090.1| (3322356), each sequence associated with the accession number is incorporated herein by reference in its entirety.

Pyruvate-formate lyase (formate acetyltransferase) is an enzyme that catalyzes the conversion of pyruvate to acetyl-coA and formate. It is induced by pfl-activating enzyme under anaerobic conditions by generation of an organic free radical and decreases significantly during phosphate limitation. A decrease or modification of the expression or activity of formate acetyltransferase in a transformed host cell can be useful in the presently disclosed methods for the production of isobutanol. Formate acetyltransferase is encoded in *E. coli* by pflB. PFLB homologs and variants are known. Such homologs and variants include, for example, formate acetyltransferase 1 (Pyruvate formate-lyase 1) gi|129879|sp|P09373.2|PFLB_ECOLI(129879); formate acetyltransferase 1 (*Yersinia pestis* CO92) gi|16121663|ref|NP_404976.1|(16121663); formate acetyltransferase 1 (*Yersinia pseudotuberculosis* IP 32953) gi|51595748|ref|YP_069939.1|(51595748); formate acetyltransferase 1 (*Yersinia pestis* biovar Microtus str. 91001) gi|45441037|ref|NP_992576.1|(45441037); formate acetyltransferase 1 (*Yersinia pestis* CO92) gi|115347142|emb|CAL20035.1|(115347142); formate acetyltransferase 1 (*Yersinia pestis* biovar Microtus str. 91001) gi|45435896|gb|AAS61453.1|(45435896); formate acetyltransferase 1 (*Yersinia pseudotuberculosis* IP 32953) gi|51589030|emb|CAH20648.1|(51589030); formate acetyltransferase 1 (*Salmonella enterica* subsp. *enterica* serovar Typhi str. CT18) gi|16759843|ref|NP_455460.1|(16759843); formate acetyltransferase 1 (*Salmonella enterica* subsp. *enterica* serovar Paratyphi A str. ATCC 9150) gi|56413977|ref|YP_151052.1|(56413977); formate acetyltransferase 1 (*Salmonella enterica* subsp. *enterica* serovar Typhi) gi|16502136|emb|CAD05373.1|(16502136); formate acetyltransferase 1 (*Salmonella enterica* subsp. *enterica* serovar Paratyphi A str. ATCC 9150) gi|56128234|gb|AAV77740.1|(56128234); formate acetyltransferase 1 (*Shigella dysenteriae* Sd197) gi|82777577|ref|YP_403926.1|(82777577); formate acetyltransferase 1 (*Shigella flexneri* 2a str. 2457T) gi|30062438|ref|NP_836609.1|(30062438); formate acetyltransferase 1 (*Shigella flexneri* 2a str. 2457T) gi|30040684|gb|AAP16415.1|(30040684); formate acetyltransferase 1 (*Shigella flexneri* 5 str. 8401) gi|110614459|gb|ABF03126.1|(110614459); formate acetyltransferase 1 (*Shigella dysenteriae* Sd197) gi|81241725|gb|ABB62435.1|(81241725); formate acetyltransferase 1 (*Escherichia coli* O157:H7 EDL933) gi|12514066|gb|AAG55388.1|AE005279_8(12514066); formate acetyltransferase 1 (*Yersinia pestis* KIM) gi|22126668|ref|NP_670091.1|(22126668); formate acetyltransferase 1 (*Streptococcus agalactiae* A909) gi|76787667|ref|YP_330335.1|(76787667); formate acetyltransferase 1 (*Yersinia pestis* KIM) gi|21959683|gb|AAM86342.1|AE013882_3(21959683); formate acetyltransferase 1 (*Streptococcus agalactiae* A909) gi|76562724|gb|ABA45308.1|(76562724); formate acetyltransferase 1 (*Yersinia enterocolitica* subsp. *enterocolitica* 8081) gi|123441844|ref|YP_001005827.1|(123441844); formate acetyltransferase 1 (*Shigella flexneri* 5 str. 8401) gi|110804911|ref|YP_688431.1|(110804911); formate acetyltransferase 1 (*Escherichia coli* UTI89) gi|91210004|ref|YP_539990.1|(91210004); formate acetyltransferase 1 (*Shigella boydii* Sb227) gi|82544641|ref|YP_408588.1|(82544641); formate acetyltransferase 1 (*Shigella sonnei* Ss046) gi|74311459|ref|YP_309878.1|(74311459); formate acetyltransferase 1 (*Klebsiella pneumoniae* subsp. *pneumoniae* MGH 78578) gi|152969488|ref|YP_001334597.1|(152969488); formate acetyltransferase 1 (*Salmonella enterica* subsp. *enterica* serovar Typhi Ty2) gi|29142384|ref|NP_805726.1|(29142384) formate acetyltransferase 1 (*Shigella flexneri* 2a str. 301) gi|24112311|ref|NP_706821.1| (24112311); formate acetyltransferase 1 (*Escherichia coli* O157:H7 EDL933) gi|15800764|ref|NP_286778.1|(15800764); formate acetyltransferase 1 (*Klebsiella pneumoniae* subsp. *pneumoniae* MGH 78578) gi|150954337|gb|ABR76367.1|(150954337); formate acetyltransferase 1 (*Yersinia pestis* CA88-4125) gi|149366640|ref|ZP_01888674.1|(149366640); formate acetyltransferase 1 (*Yersinia pestis* CA88-4125) gi|149291014|gb|EDM41089.1|(149291014); formate acetyltransferase 1 (*Yersinia enterocolitica* subsp. *enterocolitica* 8081) gi|122088805|emb|CAL11611.1| (122088805); formate acetyltransferase 1 (*Shigella sonnei* Ss046) gi|73854936|gb|AAZ87643.1|(73854936); formate acetyltransferase 1 (*Escherichia coli* UTI89) gi|91071578|gb|ABE06459.1|(91071578); formate acetyltransferase 1 (*Salmonella enterica* subsp. *enterica* serovar Typhi Ty2) gi|29138014|gb|AAO69575.1|(29138014); formate acetyltransferase 1 (*Shigella boydii* Sb227) gi|81246052|gb|ABB66760.1|(81246052); formate acetyltransferase 1 (*Shigella flexneri* 2a str. 301) gi|24051169|gb|AAN42528.1|(24051169); formate acetyltransferase 1 (*Escherichia coli* O157:H7 str. Sakai) gi|13360445|dbj|BAB34409.1|(13360445); formate acetyltransferase 1 (*Escherichia coli* O157:H7 str. Sakai) gi|15830240|ref|NP_309013.1|(15830240); formate acetyltransferase I (pyruvate formate-lyase 1) (*Photorhabdus luminescens* subsp. *laumondii* TTO1) gi|36784986|emb|CAE13906.1|(36784986); formate acetyltransferase I (pyruvate formate-lyase 1) (*Photorhabdus luminescens* subsp. *laumondii* TTO1) gi|37525558|ref|NP_928902.1|(37525558); formate acetyltransferase (*Staphylococcus aureus* subsp. *aureus* Mu50) gi|14245993|dbj|BAB56388.1|(14245993); formate acetyltransferase (*Staphylococcus aureus* subsp. *aureus* Mu50) gi|15923216|ref|NP_370750.1|(15923216); formate acetyltransferase (pyruvate formate-lyase) gi|81706366|sp|Q7A7X6.1|PFLB_STAAN(81706366); formate acetyltransferase (pyruvate formate-lyase) gi|81782287|sp|Q99WZ7.1|PFLB_STAAM(81782287); formate acetyltransferase (pyruvate formate-lyase) gi|81704726|sp|Q7A1W9.1|PFLB_STAAW(81704726); formate acetyltransferase (*Staphylococcus aureus* subsp. *aureus* Mu3) gi|156720691| dbj|BAF77108.1|(156720691); formate acetyltransferase (*Erwinia carotovora* subsp. *atroseptica* SCRI1043) gi|50121521|ref|YP_050688.1| (50121521); formate acetyltransferase (*Erwinia carotovora* subsp. *atroseptica* SCRI1043) gi|49612047|emb|CAG75496.1|(49612047); formate acetyltransferase (*Staphylococcus aureus* subsp. *aureus* str. Newman) gi|150373174| dbj|BAF66434.1|(150373174); formate acetyltransferase (*Shewanella oneidensis* MR-1) gi|24374439|ref|NP_718482.1|(24374439); formate acetyltransferase (*Shewanella oneidensis* MR-1) gi|24349015|gb|AAN55926.1|E015730_3 (24349015); formate acetyltransferase (*Actinobacillus pleuropneumoniae* serovar 3 str. JL03) gi|165976461|ref|YP_001652054.1| (165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. *aureus* MW2) gi|21203365|dbj|BAB94066.1|(21203365); formate acetyltransferase (*Staphylococcus aureus* subsp. *aureus* N315) gi 113700141|dbj|BAB41440.1|(13700141); formate acetyltransferase (*Staphylococcus aureus* subsp. *aureus* str. Newman) gi|151220374|ref|YP_001331197.1| (151220374); formate acetyltransferase (*Staphylococcus aureus* subsp. *aureus* Mu3) gi|156978556|ref|YP_001440815.1|(156978556); formate acetyltransferase (*Synechococcus* sp. JA-2-3B'a(2-13)) gi|86607744|ref|YP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1| (116517188); formate acetyltransferase (*Synechococcus* sp. JA-2-3B'a(2-13)) gi|86556286|gb|ABD01243.1| (86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. *aureus* MRSA252) gi|49482458|ref|YP_039682.1|(49482458); and formate acetyltransferase (*Staphylococcus aureus* subsp. *aureus* MRSA252) gi|49240587|emb|CAG39244.1| (49240587), each sequence associated with the accession number is incorporated herein by reference in its entirety.

Alpha isopropylmalate synthase (EC 2.3.3.13, sometimes referred to a 2-isopropylmalate synthase, alpha-IPM synthetase) catalyzes the condensation of the acetyl group of acetyl-CoA with 3-methyl-2-oxobutanoate (2-oxoisovalerate) to form 3-carboxy-3-hydroxy-4-methylpentanoate (2-isopropylmalate). Alpha isopropylmalate synthase is encoded in *E. coli* by leuA. LeuA homologs and variants are known. Such homologs and variants include, for example, 2-isopropylmalate synthase (*Corynebacterium glutamicum*) gi|452382|emb|CAA50295.1|(452382); 2-isopropylmalate synthase (*Escherichia coli* K12) gi|16128068|ref|NP_414616.1|(16128068); 2-isopropylmalate synthase (*Escherichia coli* K12) gi|1786261|gb|AAC73185.1|(1786261); 2-isopropylmalate synthase (*Arabidopsis thaliana*) gi|15237194|ref|NP_197692.1|(15237194); 2-isopropylmalate synthase (*Arabidopsis thaliana*) gi|42562149|ref|NP_173285.2|(42562149); 2-isopropylmalate synthase (*Arabidopsis thaliana*) gi|15221125|ref|NP_177544.1|(15221125); 2-isopropylmalate synthase (*Streptomyces coelicolor* A3(2)) gi|321411731 ref|NP_733575.1|(32141173); 2-isopropylmalate synthase (*Rhodopirellula baltica* SH 1) gi|32477692|ref|NP_870686.1|(32477692); 2-isopropylmalate synthase (*Rhodopirellula baltica* SH 1) gi|32448246|emb|CAD77763.1|(32448246); 2-isopropylmalate synthase (*Akkermansia muciniphila* ATCC BAA-835) gi|166241432|gb|EDR53404.1|(166241432); 2-isopropylmalate synthase (*Herpetosiphon aurantiacus* ATCC 23779) gi|159900959|ref|YP_001547206.1|(159900959); 2-isopropylmalate synthase (*Dinoroseobacter shibae* DFL 12) gi|159043149|ref|YP_001531943.1|(159043149); 2-isopropylmalate synthase (*Salinispora arenicola* CNS-205) gi|159035933|ref|YP_001535186.1|(159035933); 2-isopropylmalate synthase (*Clavibacter michiganensis* subsp. *michiganensis* NCPPB 382) gi|148272757|ref|YP_001222318.1|(148272757); 2-isopropylmalate synthase (*Escherichia coli* B) gi|124530643|ref|ZP_01701227.1| (124530643); 2-isopropylmalate synthase (*Escherichia coli* C str. ATCC 8739) gi|124499067|gb|EAY46563.1| (124499067); 2-isopropylmalate synthase (*Bordetella pertussis* Tohama I) gi|33591386|ref|NP_879030.1| (33591386); 2-isopropylmalate synthase (*Polynucleobacter necessarius* STIR1) gi|164564063|ref|ZP_02209880.1| (164564063); 2-isopropylmalate synthase (Polynucleobacter necessarius STIR1) gi|164506789|gb|EDQ94990.1| (164506789); and 2-isopropylmalate synthase (*Bacillus weihenstephanensis* KBAB4) gi|163939313|ref|YP_001644197.1|(163939313), any sequence associated with the accession number is incorporated herein by reference in its entirety.

BCAA aminotransferases catalyze the formation of branched chain amino acids (BCAA). A number of such aminotransferases are known and are exemplified by ilvE in *E. coli*. A reduction in the expression or activity or some aminotransferases in a host cell, such as, ilvE can be advantageous in the methods of the present disclosure. Exemplary homologs and variants include sequences designated by the following accession numbers: ilvE (*Microcystis aeruginosa* PCC 7806) gi|159026756|emb|CA086637.1|(159026756); IlvE (*Escherichia coli*) gi|87117962|gb|ABD20288.1| (87117962); IlvE (*Escherichia coli*) gi|87117960|gb|ABD20287.1|(87117960); IlvE (*Escherichia coli*) gi|87117958|gb|ABD20286.1|(87117958); IlvE (*Shigella flexneri*) gi|87117956|gb|ABD20285.1| (87117956); IlvE (*Shigella flexneri*) gi|87117954|gb|ABD20284.1|(87117954); IlvE (*Shigella flexneri*) gi|87117952|gb|ABD20283.1|(87117952); IlvE (*Shigella flexneri*) gi|87117950|gb|ABD20282.1| (87117950); IlvE (*Shigella flexneri*) gi|87117948|gb|ABD20281.1|(87117948); IlvE (*Shigella flexneri*) gi|87117946|gb|ABD20280.1|(87117946); IlvE (*Shigella flexneri*) gi|87117944|gb|ABD20279.1| (87117944); IlvE (*Shigella flexneri*) gi|87117942|gb|ABD20278.1|(87117942); IlvE (*Shigella flexneri*) gi|87117940|gb|ABD20277.1|(87117940); IlvE (*Shigella flexneri*) gi|87117938|gb|ABD20276.1| (87117938); IlvE (*Shigella dysenteriae*) gi|87117936|gb|ABD20275.1|(87117936); IlvE (*Shigella dysenteriae*) gi|87117934|gb|ABD20274.1|(87117934); IlvE (*Shigella dysenteriae*) gi|87117932|gb|ABD20273.1| (87117932); IlvE (*Shigella dysenteriae*) gi|87117930|gb|ABD20272.1|(87117930); and IlvE (*Shigella dysenteriae*) gi|87117928|gb|ABD20271.1| (87117928), each sequence associated with the accession number is incorporated herein by reference.

Tyrosine aminotransferases catalyzes transamination for both dicarboxylic and aromatic amino-acid substrates. A tyrosine aminotransferase of *E. coli* is encoded by the gene tyrB. A reduction in the expression or activity or some aminotransferases in a host cell, such as, TyrB can be advantageous in the methods of the present disclosure. TyrB homologs and variants are known. For example, such homologs and variants include tyrB (*Bordetella petrii*) gi|163857093|ref|YP_001631391.1|(163857093); tyrB (*Bordetella petrii*) gi|163260821|emb|CAP43123.1| (163260821); aminotransferase gi|551844|gb|AAA24704.1| (551844); aminotransferase (*Bradyrhizobium* sp. BTAi1) gi|146404387|gb|ABQ32893.1|(146404387); tyrosine aminotransferase TyrB (*Salmonella enterica*) gi|4775574|emb|CAB40973.2|(4775574); tyrosine aminotransferase (*Salmonella typhimurium* LT2) gi|16422806|gb|AAL23072.1|(16422806); and tyrosine aminotransferase gi|148085|gb|AAA24703.1|(148085), each sequence of which is incorporated herein by reference.

Pyruvate oxidase catalyzes the conversion of pyruvate to acetate and $CO_2$. In *E. coli*, pyruvate oxidase is encoded by poxB. A reduction in the expression or activity or some aminotransferases in a host cell, such as, PoxB can be advantageous in the methods of the present disclosure. PoxB and homologs and variants thereof include, for example, pyruvate oxidase; PoxB (*Escherichia coli*) gi|685128|gb|AAB31180.1|bbm|348451|bbs|154716 (685128); PoxB (*Pseudomonas fluorescens*) gi|32815820|gb|AAP88293.1|(32815820); poxB (*Escherichia coli*) gi|25269169|emb|CAD57486.1|(25269169); pyruvate dehydrogenase (*Salmonella enterica* subsp. *enterica* serovar Typhi) gi|16502101|emb|CAD05337.1| (16502101); pyruvate oxidase (*Lactobacillus plantarum*)

gi|41691702|gb|AAS10156.1|(41691702); pyruvate dehydrogenase (*Bradyrhizobium japonicum*) gi|20257167|gb|AAM12352.1|(20257167); pyruvate dehydrogenase (*Yersinia pestis* KIM) gi|22126698|ref|NP_670121.1|(22126698); pyruvate dehydrogenase (cytochrome) (*Yersinia pestis* biovar Antigua str. B42003004) gi|166211240|ref|ZP_02237275.1|(166211240); pyruvate dehydrogenase (cytochrome) (*Yersinia pestis* biovar Antigua str. B42003004) gi|166207011|gb|EDR51491.1| (166207011); pyruvate dehydrogenase (*Pseudomonas syringae* pv. tomato str. DC3000) gi|28869703|ref|NP_792322.1| (28869703); pyruvate dehydrogenase (*Salmonella typhimurium* LT2) gi|16764297|ref|NP_459912.1| (16764297); pyruvate dehydrogenase (*Salmonella enterica* subsp. *enterica* serovar Typhi str. CT18) gi|16759808|ref|NP_455425.1|(16759808); pyruvate dehydrogenase (cytochrome) (*Coxiella burnetii* Dugway 5J108-111) gi|154706110|ref|YP_001424132.1|(154706110); pyruvate dehydrogenase (*Clavibacter michiganensis* subsp. *michiganensis* NCPPB 382) gi|148273312|ref|YP_001222873.1|(148273312); pyruvate oxidase (*Lactobacillus acidophilus* NCFM) gi|58338213|ref|YP_194798.1| (58338213); and pyruvate dehydrogenase (*Yersinia pestis* CO92) gi|16121638|ref|NP_404951.1|(16121638), the sequences of each accession number are incorporated herein by reference.

L-threonine 3-dehydrogenase (EC 1.1.1.103) catalyzes the conversion of L-threonine to L-2-amino-3-oxobutanoate. The gene tdh encodes an L-threonine 3-dehydrogenase. There are approximately 700 L-threonine 3-dehydrogenases from bacterial organism recognized in NCBI. Various homologs and variants of tdh include, for example, L-threonine 3-dehydrogenase gi|135560|sp|P07913.1|TDH_ECOLI (135560); L-threonine 3-dehydrogenase gi|166227854|sp|A4TSC6.1|TDH_YERPP(166227854); L-threonine 3-dehydrogenase gi|166227853|sp|A1JHX8.1|TDH_YERE8 (166227853); L-threonine 3-dehydrogenase gi|166227852|sp|A6UBM6.1|TDH_SINMW(166227852); L-threonine 3-dehydrogenase gi|16622785|sp|A1RE07.1|TDH_SHESW(166227851); L-threonine 3-dehydrogenase gi|166227850|sp|A0L2Q3.1|TDH_SHESA(166227850); L-threonine 3-dehydrogenase gi|166227849|sp|A4YCC5.1|TDH_SHEPC(166227849); L-threonine 3-dehydrogenase gi|166227848|sp|A3QJC8.1|TDH_SHELP(166227848); L-threonine 3-dehydrogenase gi|166227847|sp|A6WUG6.1|TDH_SHEB8(166227847); L-threonine 3-dehydrogenase gi|166227846|sp|A3CYN0.1|TDH_SHEB5 (166227846); L-threonine 3-dehydrogenase gi|166227845|sp|A1S1Q3.1|TDH_SHEAM(166227845); L-threonine 3-dehydrogenase gi|166227844|sp|A4FND4.1|TDH_SACEN(166227844); L-threonine 3-dehydrogenase gi|166227843|sp|A1SVW5.1|TDH_PSYIN(166227843); L-threonine 3-dehydrogenase gi|166227842|sp|A51GK7.1|TDH_LEGPC(166227842); L-threonine 3-dehydrogenase gi|166227841|sp|A6TFL2.1|TDH_KLEP7 (166227841); L-threonine 3-dehydrogenase gi|166227840|sp|A41Z92.1|TDH_FRATW(166227840); L-threonine 3-dehydrogenase gi|166227839|sp|A0Q5K3.1|TDH_FRATN(166227839); L-threonine 3-dehydrogenase gi|166227838|sp|A7NDM9.1|TDH_FRATF(166227838); L-threonine 3-dehydrogenase gi|166227837|sp|A7MID0.1|TDH_ENTS8(166227837); and L-threonine 3-dehydrogenase gi|166227836|sp|A1AHF3.1|TDH_ECOK1 (166227836), the sequences associated with each accession number are incorporated herein by reference.

Acetohydroxy acid synthases and acetolactate synthases (e.g., alsS) catalyze the synthesis of the branched-chain amino acids (valine, leucine, and isoleucine). IlvH encodes an acetohydroxy acid synthase in *E. coli* (see, e.g., acetohydroxy acid synthase AHAS III (IlvH) (*Escherichia coli*) gi|40846|emb|CAA38855.1|(40846), incorporated herein by reference). Homologs and variants as well as operons comprising ilvH are known and include, for example, ilvH (*Microcystis aeruginosa* PCC 7806) gi|159026908|emb|CA089159.1|(159026908); IlvH (*Bacillus amyloliquefaciens* FZB42) gi|154686966|ref|YP_001422127.1|(154686966); IlvH (*Bacillus amyloliquefaciens* FZB42) gi|154352817|gb|ABS74896.1|(154352817); IlvH (*Xenorhabdus nematophila*) gi|131054140|gb|ABO32787.1|(131054140); IlvH (*Salmonella typhimurium*) gi|7631124|gb|AAF65177.1|AF117227_2(7631124), ilvN (*Listeria innocua*) gi|16414606|emb|CAC97322.1| (16414606); ilvN (*Listeria monocytogenes*) gi|16411438|emb|CAD00063.1|(16411438); acetohydroxy acid synthase (*Caulobacter crescentus*) gi|408939|gb|AAA23048.1|(408939); acetohydroxy acid synthase I, small subunit (*Salmonella enterica* subsp. *enterica* serovar Typhi) gi|16504830|emb|CAD03199.11 (16504830); acetohydroxy acid synthase, small subunit (*Tropheryma whipplei* TW08/27) gi|28572714|ref|NP_789494.1|(28572714); acetohydroxy acid synthase, small subunit (*Tropheryma whipplei* TWO8/27) gi|28410846|emb|CAD67232.1|(28410846); acetohydroxy acid synthase I, small subunit (*Salmonella enterica* subsp. *enterica* serovar Paratyphi A str. ATCC 9150) gi|56129933|gb|AAV79439.1|(56129933); acetohydroxy acid synthase small subunit; (*Cornybacterium glutamicum*) gi|551779|gb|AAA62430.1|(551779); acetohydroxy acid synthase I, small subunit (*Salmonella enterica* subsp. *enterica* serovar Typhi Ty2) gi|29139650|gb|AA071216.1| (29139650); acetohydroxy acid synthase small subunit (*Streptomyces cinnamonensis*) gi|5733116|gb|AAD49432.1|AF175526_1(5733116); and acetohydroxy acid synthase, large subunit (*Cornybacterium glutamicum*) gi|400334|gb|AAA62429.1|(400334), the sequences associated with the accession numbers are incorporated herein by reference.

Acetolactate synthase genes include alsS and ilvI. ALS protein which have both acetolactate synthase activity and decarboxylase activity are useful in the methods of the present disclosure. Homologs of ilvI and alsS are known and can be tested for this dual activity. In addition, the structure of the known proteins can be compared with that of AlsS to determine homology and that likely possess the dual activity. Known homologs can include, for example, acetolactate synthase small subunit (*Bifidobacterium longum* NCC2705) gi|23325489|gb|AAN24137.1|(23325489); acetolactate synthase small subunit (*Geobacillus stearothermophilus*) gi|19918933|gb|AAL99357.1|(19918933); acetolactate synthase (*Azoarcus* sp. BH72) gi|119671178|emb|CAL95091.1| (119671178); Acetolactate synthase small subunit (*Corynebacterium diphtheriae*) gi|38199954|emb|CAE49622.1| (38199954); acetolactate synthase (*Azoarcus* sp. BH72) gi|119669739|emb|CAL93652.1|(119669739); acetolactate synthase small subunit (*Corynebacterium jeikeium* K411)

gi|68263981|emb|CAI37469.1|(68263981); acetolactate synthase small subunit (*Bacillus subtilis*) gi|1770067|emb|CAA99562.1|(1770067); acetolactate synthase isozyme 1 small subunit (AHAS-I) (acetohydroxyacid synthase I small subunit) (ALS-I) gi|83309006|sp|P0ADF8.1|ILVN_ECOLI(83309006); acetolactate synthase large subunit (*Geobacillus stearothermophilus*) gi|19918932|gb|AAL99356.1|(19918932); and acetolactate synthase, small subunit (*Thermoanaerobacter tengcongensis* MB4) gi|20806556|ref|NP_621727.1| (20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. IlvC encodes an acetohydroxy acid isomeroreductase in *E. coli*. Homologs and variants of ilvC are known and include, for example, acetohydroxyacid reductoisomerase (*Schizosaccharomyces pombe* 972h-) gi|162312317|ref|NP_001018845.2|(162312317); acetohydroxyacid reductoisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxyacid reductoisomerase (*Saccharomyces cerevisiae*) gi|609403|gb|AAB67753.1|(609403); ACL198Wp (*Ashbya gossypii* ATCC 10895) gi|45185490|ref|NP_983206.1|(45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1||bbm|369068|bbs|165406 (957238); acetohydroxy-acid isomeroreductase; Ilv5g (*Saccharomyces cerevisiae*) gi|957236|gb|AAB33578.1||bbm|369064|bbs|165405 (957236); and ketol-acid reductoisomerase (*Schizosaccharomyces pombe*) gi|2696654|dbj|BAA24000.1|(2696654), each sequence associated with the accession number is incorporated herein by reference.

Dihydroxy-acid dehydratases catalyze the fourth step in the biosynthesis of isoleucine and valine, the dehydration of 2,3-dihydroxy-isovaleic acid into alpha-ketoisovaleric acid. IlvD and ilv3 encode a dihydroxy-acid dehydratase. Homologs and variants of dihydroxy-acid dehydratases are known and include, for example, IlvD (*Mycobacterium leprae*) gi|2104594|emb|CAB08798.1|(2104594); dihydroxy-acid dehydratase (*Tropheryma whipplei* TW08/27) gi|28410848|emb|CAD67234.1|(28410848); dihydroxy-acid dehydratase (*Mycobacterium leprae*) gi|13093837|emb|CAC32140.1|(13093837); dihydroxy-acid dehydratase (*Rhodopirellula baltica* SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1| (49242408), each sequence associated with the accession numbers are incorporated herein by reference.

2-Keto acid decarboxylases catalyze the conversion of a 2-keto acid to the respective aldehyde. For example, 2-ketoisovalerate decarboxylase catalyzes the conversion of 2-ketoisovalerate to isobutyraldehyde. A number of 2-keto acid decarboxylases are known and are exemplified by the pdc, pdc1, pdc5, pdc6, aro10, thI3, kdcA and kivd genes. The Als described herein is intended to replace the 2-keto acid decarboxylase activity of this enzyme. In certain examples, a recombinant host cell does not have to be transformed with a polynucleotide that encodes a 2-keto acid decarboxylase reducing the complexity of the recombinant microorganism. Exemplary homologs and variants useful for the conversion of a 2-keto acid to the respective aldehyde comprise sequences designated by the following accession numbers and identified enzymatic activity: gi|44921617|gb|AAS49166.1|branched-chain alpha-keto acid decarboxylase (*Lactococcus lactis*); gi|15004729|ref|NP_149189.1| Pyruvate decarboxylase (*Clostridium acetobutylicum* ATCC 824); gi|82749898|ref|YP_415639.1| probable pyruvate decarboxylase (*Staphylococcus aureus* RF122); gi|77961217|ref|ZP_00825060.1| COG3961: pyruvate decarboxylase and related thiamine pyrophosphate-requiring enzymes (*Yersinia mollaretii* ATCC 43969); gi|71065418|ref|YP_264145.1| putative pyruvate decarboxylase (*Psychrobacter arcticus* 273-4); gi|16761331|ref|NP_456948.1| putative decarboxylase (*Salmonella enterica* subsp. *enterica* serovar Typhi str. CT18); gi|93005792|ref|YP_580229.1| pyruvate decarboxylase (*Psychrobacter cryohalolentis* K5); gi|23129016|ref|ZP_00110850.1| COG3961 pyruvate decarboxylase and related thiamine pyrophosphate-requiring enzymes (*Nostoc punctiforme* PCC 73102); gi|16417060|gb|AAL18557.1|AF354297_1 pyruvate decarboxylase (*Sarcina ventriculi*); gi|15607993|ref|NP_215368.1| probable pyruvate or indole-3-pyruvate decarboxylase (pdc) (*Mycobacterium tuberculosis* H37Rv); gi|41406881|ref|NP_959717.1|Pdc (*Mycobacterium avium* subsp. *paratuberculosis* K-10); gi|91779968|ref|YP_555176.1| putative pyruvate decarboxylase (*Burkholderia xenovorans* LB400); gi|15828161|ref|NP_302424.1| pyruvate (or indolepyruvate) decarboxylase (*Mycobacterium leprae* TN); gi|118616174|ref|YP_904506.1| pyruvate or indole-3-pyruvate decarboxylase (Pdc) (*Mycobacterium ulcerans* Agy99); gi|67989660|ref|NP_001018185.1| hypothetical protein SPAC3H8.01 (*Schizosaccharomyces pombe* 972h-); gi|21666011|gb|AAM73540.1|AF282847_1 pyruvate decarboxylase PdcB (*Rhizopus oryzae*); gi|69291130|ref|ZP_00619161.1| pyruvate decarboxylase: pyruvate decarboxylase (*Kineococcus radiotolerans* SRS30216); gi|66363022|ref|XP_628477.1| pyruvate decarboxylase (*Cryptosporidium parvum* Iowa II); gi|70981398|ref|XP_731481.1| pyruvate decarboxylase (*Aspergillus fumigatus* Af293); gi|121704274|ref|XP_001270401.1| pyruvate decarboxylase, putative (*Aspergillus clavatus* NRRL 1); gi|119467089|ref|XP_001257351.1| pyruvate decarboxylase, putative (*Neosartorya fischeri* NRRL 181); gi|26554143|ref|NP_758077.1| pyruvate decarboxylase (*Mycoplasma penetrans* HF-2); gi|21666009|gb|AAM73539.1|AF282846_1 pyruvate decarboxylase PdcA (*Rhizopus oryzae*).

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh 6 and sfa1 (see, e.g., SFA (*Saccharomyces cerevisiae*) gi|288591|emb|CAA48161.1|(288591); the sequence associated with the accession number is incorporated herein by reference).

Citramalate synthase catalyzes the condensation of pyruvate and acetate. CimA encodes a citramalate synthase. Homologs and variants are known and include, for example, citramalate synthase (*Leptospira biflexa* serovar Patoc) gi|116664687|gb|ABK13757.1|(116664687); citramalate synthase (*Leptospira biflexa* serovar Monteralerio) gi|116664685|gb|ABK13756.1|(116664685); citramalate synthase (*Leptospira interrogans* serovar Hebdomadis) gi|116664683|gb|ABK13755.1|(116664683); citramalate synthase (*Leptospira interrogans* serovar Pomona) gi|116664681|gb|ABK13754.1|(116664681); citramalate synthase (*Leptospira interrogans* serovar Australis) gi|116664679|gb|ABK13753.1|(116664679); citramalate synthase (*Leptospira interrogans* serovar Autumnalis) gi|116664677|gb|ABK13752.1|(116664677); citramalate synthase (*Leptospira interrogans* serovar Pyrogenes) gi|116664675|gb|ABK13751.1|(116664675); citramalate synthase (*Leptospira interrogans* serovar Canicola) gi|116664673|gb|ABK13750.1|(116664673); citramalate synthase (*Leptospira interrogans* serovar Lai) gi|116664671|gb|ABK13749.1|(116664671); CimA (*Leptospira meyeri* serovar Semaranga) gi|119720987|gb|ABL98031.1|(119720987); (R)-citramalate synthase gi|2492795|sp|Q58787.1|CIMA_METJA (2492795); (R)-citramalate synthase gi|22095547|sp|P58966.1|CIMA_METMA(22095547); (R)-citramalate synthase gi|22001554|sp|Q8TJJ1.1|CIMA_METAC(22001554); (R)-citramalate synthase gi|22001553|sp|O26819.1|CIMA_METTH(22001553); (R)-citramalate synthase gi|22001555|sp|Q8TYB1.1|CIMA_METKA(22001555); (R)-citramalate synthase (*Methanococcus maripaludis* S2) gi|45358581|ref|NP_988138.1|(45358581); (R)-citramalate synthase (*Methanococcus maripaludis* S2) gi|44921339|emb|CAF30574.1|(44921339); and similar to (R)-citramalate synthase (*Candidatus Kuenenia* stuttgartiensis) gi|91203541|emb|CAJ71194.1|(91203541), each sequence associated with the foregoing accession numbers is incorporated herein by reference.

It is understood that a range of microorganisms can be modified to include a recombinant metabolic pathway suitable for the production of e.g., 1-propanol, isobutanol, 1-butanol, 2-methyl-1-butanol, 3-methyl-1-butanol, or 2-phenylethanol. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria, and Eucarya, the latter including yeast and filamentous fungi, protozoa, algae, or higher Protista. The terms "microbial cells" and "microbes" are used interchangeably with the term "microorganism".

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ((NaCl)); and extreme (hyper) thermophilus (prokaryotes that live at very high temperatures). Besides the unifying archaeal features that distinguish them from Bacteria (i.e., no murein in cell wall, ester-linked membrane lipids, and the like), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or over-express endogenous polynucleotides, or to express non-endogenous sequences, such as those included in a vector, or which have a reduction in expression of an endogenous gene. The polynucleotide generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism. *E. coli*, Yeast, *Corynebacterium, Lactobacillus, Bacillus*, and the like, are particularly useful as a host cell.

A "parental microorganism" refers to a cell used to generate, or derive, a recombinant microorganism. The term "parental microorganism" describes a cell that occurs in nature, i.e., a "wild-type" cell that has not been genetically modified. The term "parental microorganism" also describes a cell that has been genetically modified but which does not express or over-express a target enzyme, e.g., an enzyme involved in the biosynthetic pathway for the production of a desired metabolite such as 1-propanol, isobutanol, 1-butanol, 2-methyl-1-butanol, 3-methyl-1-butanol, or 2-phenylethanol. For example, a wild-type microorganism can be genetically modified to express or over-express a first target enzyme such as acetolactate synthase. This microorganism can act as a parental microorganism in the generation of a microorganism modified to express or over-express a second target enzyme, e.g., acetohydroxy acid isomeroreductase (IlvC). In turn, the microorganism modified to express or over-express, e.g., acetolactate synthase and acetohydroxy acid isomeroreductase, can be modified to express or over-express a third target enzyme, e.g., dihydroxy-acid dehydratase (IlvD). Accordingly, a parental microorganism, or host microorganism, functions as a reference cell for successive genetic modification events. Each modification event can be accomplished by introducing a nucleic acid molecule into the reference cell. The introduction facilitates the expression or over-expression of a target enzyme. It is understood that the term "facilitates" encompasses the activation of endogenous polynucleotides encoding a target enzyme through genetic modification of, e.g., a promoter sequence in a parental microorganism. It is further understood that the term "facilitates" encompasses the introduction of exogenous polynucleotides encoding a target enzyme into a parental microorganism.

In another embodiment, a method of producing a recombinant microorganism that converts a suitable carbon substrate to, e.g., isobutanol, 2-methyl 1-butanol, and/or 3-methyl 1-butanol is provided. The method includes transforming a microorganism with one or more recombinant polynucleotides encoding polypeptides that include, for example, an enzyme having both acetolatate synthase and 2-ketodecarboxylase activity (e.g., als), and a polypeptide having alcohol dehydrogenase activity. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a nonfunctional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

It is understood that the polynucleotides described above include "genes" and that the nucleic acid molecules described above include "vectors" or "plasmids." For example, a polynucleotide encoding a polypeptide having acetolactate synthase and 2-ketodecarboxylase activity can be encoded by an als gene or homolog thereof. Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine, for example, the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophages, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

Those of skill in the art will recognize that, due to the degenerate nature of the genetic code, a variety of DNA compounds differing in their nucleotide sequences can be used to encode a given amino acid sequence (e.g., enzyme) of the disclosure. The native DNA sequence encoding the biosynthetic enzymes described herein are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and/or insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the heterologous expression of one or more of the biosynthetic genes involved in alcohol production (e.g., isobutanol production or biosynthesis and recombinant DNA expression vectors useful in the method. Thus, included within the scope of the disclosure are recombinant expression vectors that include such nucleic acids. The term "expression vector" refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1, and pBR.

A nucleic acid of the disclosure can be amplified using cDNA, mRNA, or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

In another embodiment a method for producing an alcohol, e.g., isobutanol, is provided. The method includes culturing a recombinant microorganism as provided herein in the presence of a suitable substrate and under conditions suitable for the conversion of the substrate to isobutanol. The alcohol produced by a microorganism provided herein can be detected by any method known to the skilled artisan. Such methods include mass spectrometry. Culture conditions suitable for the growth and maintenance of a recombinant microorganism provided herein are described in the Examples below. The skilled artisan will recognize that such conditions can be modified to accommodate the requirements of each microorganism.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning: A Laboratory Manual, 2d ed., Vol. 1-3, Cold Spring Harbor Laboratory, Cold Spring Harbor, N.Y., 1989 ("Sambrook"); and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) *C&EN* 36-47; The Journal Of NIH Research (1991) 3:81-94; Kwoh et al. (1989) *Proc. Natl. Acad. Sci. USA* 86:1173; Guatelli et al. (1990) *Proc. Nat'l Acad. Sci. USA* 87:1874; Lomell et al. (1989) *J. Clin. Chem.* 35:1826; Landegren et al. (1988) *Science* 241:1077-1080; Van Brunt (1990) *Biotechnology* 8:291-294; Wu and Wallace (1989) Gene 4:560; Barringer et al. (1990) Gene 89:117; and Sooknanan and Malek (1995) *Biotechnology* 13:563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369:684-685 and the references cited therein, in which PCR amplicons of up to 40 kb are generated. One of skill will appreciate that essentially any RNA can be converted into a double stranded DNA suitable for restriction digestion, PCR expansion, and sequencing using reverse transcriptase and a polymerase. See, e.g., Ausubel, Sambrook and Berger, all supra.

Appropriate culture conditions are conditions of culture medium pH, ionic strength, nutritive content, and the like; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

The invention is illustrated in the following examples, which are provided by way of illustration and are not intended to be limiting.

EXAMPLES

Restriction enzymes and Antarctic phosphatase were from New England Biolabs (Ipswich, Mass.). The rapid DNA ligation kit was from Roche (Manheim, Germany). KOD DNA polymerase was from EMD Chemicals (San Diego, Calif.). Oligonucleotides were from Operon (Huntsville, Ala.).

Strains and plasmids. A list of many of the strains, plasmids, and oligos used is given in Table 1. JCL16 (Atsumi et al., (2008) *Metab. Eng.* 10:305-311) is BW25113 (rrn$_{T14}$ ΔlacZ$_{WJ16}$ hsdR514 ΔaraBAD$_{AH33}$ ΔrhaBAD$_{LD78}$) (Datsenko and Wanner, (2000) *Proc. Natl. Acad. Sci. USA* 97:6640-6645) with F' transduced from XL-1 Blue to supply lacIq. JCL260 is JCL16 ΔadhE Δfnr-ldhA ΔfrdBC ΔpflB Δpta. The ilvC gene was inactivated by P1 transduction with JW3747 (Baba et al., (2006) *Mol. Syst. Biol.* 2:2006.0008, doi:10.1038/msb4100050).

References: (A) Datsenko and Wanner, (2000) *Proc. Natl. Acad. Sci. USA* 97:6640-6645; (B) Atsumi et al., (2008) *Metab. Eng.* 10:305-311; (C) Atsumi et al., (2008) *Nature* 451:86-89; (D) Atsumi and Liao, (2008) *Appl. Environ. Microbiol.* 74:7802-78081; (E) Shen and Liao, (2008) *Metab. Eng.* 10:312-320.

To clone alsS, pSA69 (Atsumi et al., (2008) *Nature* 451: 86-89) was digested with AatII and SalI. A shorter fragment was purified and cloned into plasmid pCS27 (Shen and Liao, (2008) *Metab. Eng.* 10:312-320) cut with the same enzymes, creating pZL8. Both alsS single site mutations (Q487N and Q487A) were introduced using PCR directed mutagenesis. To introduce the mutation into alsS, pSA69 was used as PCR template with A306 and A124 (Q487N) and A307 and A124 (Q487A). The beginning of the alsS gene located on pSA69 was also amplified from the AatII site upstream of the ribosome binding site to the 1,485th base in the alsS gene, using primers A300 and A305. These two fragments were then

TABLE 1

Strains, plasmids and oligos used in the Examples

| | Relevant Genotype | Reference |
|---|---|---|
| Strain | | |
| BW25113 | rrn$_{BT14}$ ΔlacZWJ16 hsdR514 ΔaraBAD$_{AH33}$ ΔrhaBAD$_{LD78}$ | (A) |
| JCL16 | BW25113/F' [traD36 proAB$^+$, lacI$^q$ ZΔM15] | (B) |
| JCL260 | Same as JCL16 but ΔadhE Δfnr-ldhA ΔfrdBC ΔpflB Δpta | (C) |
| SA296 | Same as JCL260 but ΔilvC | This work |
| KS145 | Same as JCL16 but ΔilvI ΔilvB | (D) |
| Plasmid | | |
| pSA55 | ColE1 ori; Amp$^r$; P$_L$lacO$_1$::kivd-ADH2 | (C) |
| pSA69 | p15A ori; Kan$^r$; P$_L$lacO$_1$::alsS-ilvC-ilvD | (C) |
| pCS27 | p15A ori; Kan$^r$; P$_L$lacO1::MCS1 | (E) |
| pZL8 | p15A ori; Kan$^R$; P$_L$lacO$_1$:: alsS | This work |
| pSA159 | Derivative of pPETDuet-1 with alsS | This work |
| pSA166 | Derivative of pPETDuet-1 with alsS(Q487A) | This work |
| pSA187 | Derivative of pETDUET-1 with alsS(Q487I) | This work |
| pSA188 | Derivative of pETDUET-1 with alsS(Q487S) | This work |
| pSA205 | Derivative of pETDUET-1 with alsS(Q487G) | This work |
| pSA206 | Derivative of pETDUET-1 with alsS(Q487L) | This work |
| Oligo | Sequence 5'→3' | |
| A124 | ACGCAGTCGACCTAGAGAGCTTTCGTTTTCATGAGT (SEQ ID NO: 11) | (C) |
| A297 | CGGGATCCGTTGACAAAAGCAACAAAAGAACAAA (SEQ ID NO: 12) | This work |
| A298 | ACGCAGTCGACCTAGAGAGCTTTCGTTTTCATGAGT (SEQ ID NO: 13) | This work |
| A300 | AATAAGACGTCTAAGAAACCATTATTATCATG (SEQ ID NO: 14) | This work |
| A305 | GAATGCAACCATGTCATATGTGCTG (SEQ ID NO: 15) | This work |
| A306 | ATGGAACGACAGCACATATGACATGGTTGCATTCAACCAATTG AAAAAA TATAACCGTAC (SEQ ID NO: 16) | This work |
| A307 | ATGGAACGACAGCACATATGACATGGTTGCATTCGCCCAATTG AAAAAA TATAACCGTAC SEQ ID NO: 17) | This work | joined by splice overlap extension (SOE). The products were digested with AatII and SalI and cloned into pSA69 cut with the same enzyme, creating pSA163 and pSA164.

For protein over-expression and purification, the wild-type and alsS variants were amplified with primers A297 and A298. PCR products were digested with BamHI and SalI and cloned into pETDuet-1 (Novagen (Madison, Wis.)) cut with the same enzymes (Table 2), creating pS159 and pSA166.

extrapolated after nonlinear regression of the experimental points with the Gauss-Newton method using Matlab.

Kdc activity assay. The enzyme assay for Kdc activity of AlsS was carried out in reaction mixtures containing 80 nM AlsS, 100 mM MOPS (pH 7.0), 1 mM $MgCl_2$, 0.1 mM TPP, 10 mM acetate, and various concentrations of KIV at 37° C. for 1 h. The production of isobutyraldehyde was confirmed to be linear over 1 h. Isobutyraldehyde was measured by a gas

TABLE 2

Kinetic parameters of the wild-type AlsS (*B. subtilis*) and the variants for acetolactate synthase and decarboxylase activity[a]

| Amino acid at residue 487 | Pyruvate | | | KIV | | |
|---|---|---|---|---|---|---|
| | $K_m$ (mM) | $k_{cat}$ ($s^{-1}$) | $k_{cat}/K_m$ ratio | $K_m$ (mM) | $k_{cat}$ ($s^{-1}$) | $k_{cat}/K_m$ ratio |
| Q | 13.6 ± 0.8 | 121 ± 13 | 8.9 ± 1.1 | 300 ± 35 | 8.9 ± 1.2 | 0.03 ± 0.005 |
| A | 8.7 ± 0.5 | 58 ± 8 | 6.7 ± 1.0 | 186 ± 27 | 1.1 ± 0.5 | 0.006 ± 0.003 |
| G | 1.6 ± 0.4 | 11 ± 5 | 6.9 ± 3.6 | 175 ± 18 | 0.8 ± 0.2 | 0.005 ± 0.001 |
| S | 1.1 ± 0.6 | 11 ± 6 | 10 ± 7.7 | 154 ± 21 | 0.8 ± 0.3 | 0.005 ± 0.002 |
| L | ND | ND | ND | 342 ± 45 | 5.4 ± 0.9 | 0.02 ± 0.003 |
| I | ND | ND | ND | 323 ± 26 | 4.8 ± 0.5 | 0.01 ± 0.002 |

[a]The values shown after the ± signs are standard deviations.
ND, not detectable.

Medium and culture conditions for isobutanol production. M9 medium (64 g $Na_2HPO_4.7H_2O$, 15 g $KH_2PO_4$, 2.5 g NaCl, 5 g $NH_4Cl$, 2 mM $MgSO_4$, 0.1 mM $CaCl_2$, 10 mg thiamine per liter water) containing 36 g/L glucose, 5 g/L yeast extract, 100 μg/ml ampicillin, 30 μg/ml kanamycin and 1 ml/liter of Trace Metal Mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water) was used for cell growth. Preculture in test tubes containing 3 ml of medium was performed at 37° C. overnight on a rotary shaker (250 rpm). Overnight culture was diluted 1:100 into 20 ml of fresh medium in a 250 ml screw cap conical flask. Cells were grown at 37° C. for 3 hrs, followed by adding 0.1 mM IPTG (isopropyl-β-D-thiogalactopyranoside). Production was performed under microaerobic conditions at 30° C. on a rotary shaker (250 rpm) for 24 hrs. Isobutanol was quantified by a gas chromatography-flame ionization detector as previously described (Atsumi et al., (2008) *Nature* 451:86-89). Secreted pyruvate was quantified by high-performance liquid chromatography as previously described (Atsumi et al., (2008) *Metab. Eng.* 10:305-311).

Protein purification. The wild type AlsS and AlsS variants were synthesized from a His-tag plasmid in *E. coli* strain BL21 Star™ (DE3) (Invitrogen (Carlsbad, Calif.)) followed by purification with Ni-nitrilotriacetic acid (NTA) spin columns (Qiagen (Valencia, Calif.)). Protein concentrations were determined by the Bradford assay (Bio-Rad (Hercules, Calif.)).

Als enzyme activity. An enzyme assay for Als activity of AlsS was carried out in 1 ml of morpholinepropanesulfonic acid (MOPS) buffer (pH 7.0) containing 80 nM AlsS, 100 mM MOPS (pH 7.0), 1 mM $MgCl_2$, 0.1 mM TPP, 10 mM acetate, and various concentrations of pyruvate at 37° C. for 10 min. The reaction was terminated by acidification of the solution with 0.1 ml of 50% $H_2SO_4$. The mixture was incubated for an additional 25 min at 37° C. to allow for the acid hydrolysis of the acetolactate to acetoin. Acetoin formation was measured as described previously (Holtzclaw and Chapman, (1975) *J. Bacteriol.* 121:917-922). One unit of enzyme activity was defined as the amount of enzyme that converts 1 μmol of substrate into product in 1 minute under these conditions. The $K_m$ values for pyruvate and the $V_{max}$ were chromatography-flame ionization detector as previously described (Atsumi et al., (2008) *Nature* 451:86-89). One unit of enzyme activity was defined as the amount of enzyme that converts 1 μmol of substrate into product in 1 minute under these conditions. The $K_m$ values for KIV and the $V_{max}$ were extrapolated after nonlinear regression of the experimental points with the Gauss-Newton method using Matlab.

TABLE 3

Sequences of included sequence listing.

| SEQ ID NO: | Comment |
|---|---|
| 1 | DNA sequence of acetolactate synthase (*B. subtilis*) |
| 2 | Protein sequence of acetolactate synthase (*B. subtilis*) |
| 3 | DNA sequence of acetolactate synthase (*B. subtilis*) where the first g is changed to a |
| 4 | Protein sequence of acetolacate synthase (*B. subtilis*) where the first amino acid is M instead of V |
| 5 | DNA sequence of acetolactate synthase Q487N mutant (mutant of SEQ ID NO: 3) |
| 6 | Protein sequence of acetolactate synthase Q487N mutant (mutant of SEQ ID NO: 5) |
| 7 | Protein sequence of acetolactate synthase Q487N mutant (mutant of SEQ ID NO: 2) |
| 8 | DNA sequence of acetolactate synthase Q487A mutant (mutant of SEQ ID NO: 1) |
| 9 | Protein sequence of acetolactate synthase Q487A mutant (mutant of SEQ ID NO: 4) |
| 10 | Protein sequence of acetolactate synthase Q487A mutant (mutant of SEQ ID NO: 2) |
| 11 | See Table 1 |
| 12 | See Table 1 |
| 13 | See Table 1 |
| 14 | See Table 1 |
| 15 | See Table 1 |
| 16 | See Table 1 |
| 17 | See Table 1 |

Analysis of the Kdc-independent isobutanol production. Since *E. coli* does not have any Kdc, it was hypothesized that pyruvate dehydrogenase (PDH) or 2-ketoglutarate dehydrogenase (KGDH) of *E. coli* could catalyze the conversion of KIV to isobutyryl coenzyme A, followed by the conversion of isobutyryl coenzyme A to isobutyraldehyde and then isobutanol by aldehyde and alcohol dehydrogenases. To test these possibilities, aceE and sucA were deleted, which encode subunits of the PDH and KGDH complexes, respectively. However, this double knockout strain with over-expression of alsS, ilvC, and ilvD was still capable of producing isobutanol, indicating that neither PDH nor KGDH catalyzes the reaction in the Kdc-independent isobutanol production.

Figure 2A:
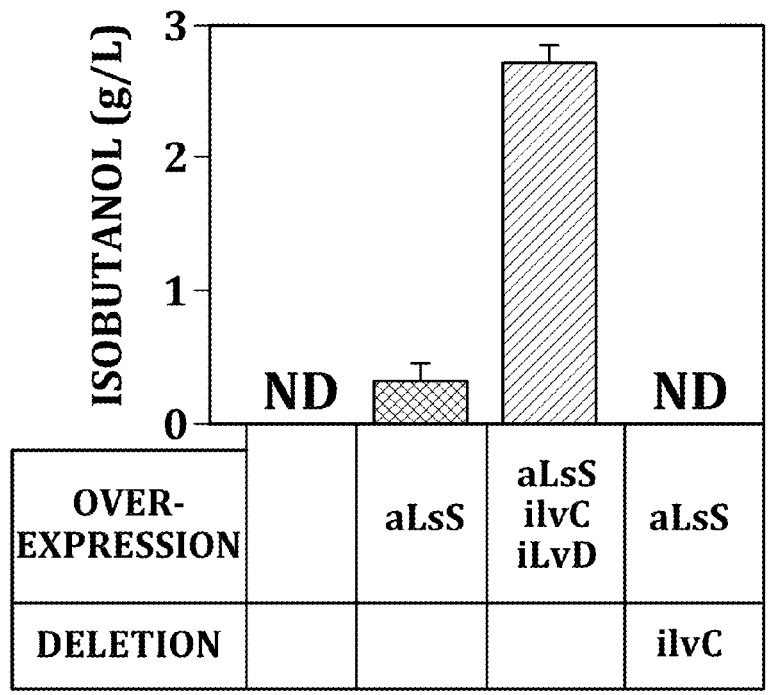
FIGS. 2A-C shows a summary of results for isobutanol production without Kdc in *E. coli*. The cells were grown in M9 medium containing 5 g/liter yeast extract and 36 g/liter glucose in shake flasks at 30° C. with 0.1 mM IPTG for 24 hrs. Over-expressed and deleted genes and KIV supplementation are indicated below the graphs.

To determine essential components for the Kdc-independent isobutanol production, isobutanol production from the strain over-expressing different combinations of alsS, ilvC, and ilvD was measured (FIG. 2). The strain over-expressing alsS alone produced isobutanol, but the strain over-expressing ilvC and ilvD did not (FIG. 2A). When ilvC and ilvD were over-expressed with alsS, isobutanol production increased nearly ninefold (FIG. 2A). Because the only known activity of AlsS is acetolactate synthase, it is unclear how the strain could produce isobutanol only with alsS over-expression. As a control experiment, ilvI and ilvH (E. coli), which encodes an acetohydroxy acid synthase (Ahas) instead of AlsS (B. subtilis), were over-expressed. The strain over-expressing ilvI and ilvH (E. coli) did not produce isobutanol. Increasing AlsS levels in E. coli led to a parallel increase in the formation of acetoin, which is the product of spontaneous decarboxylation of 2-acetolactate (Aristidou et al., (1994) Biotechnol. Bioeng. 44:944-951). To test whether some enzymes in E. coli could utilize acetoin as a substrate for isobutanol production, acetoin was fed to the E. coli culture. Neither isobutyraldehyde nor isobutanol was detected from this culture, indicating that acetoin was not a precursor of isobutanol in this pathway. To confirm that the Kdc-independent pathway used the same route as the Kdc-dependent pathway, the ilvC gene on the genome was deleted (FIG. 2A). The deletion of ilvC abolished isobutanol production, indicating that this Kdc-independent pathway utilized KIV as a precursor (FIG. 2A).

Figure 2B:
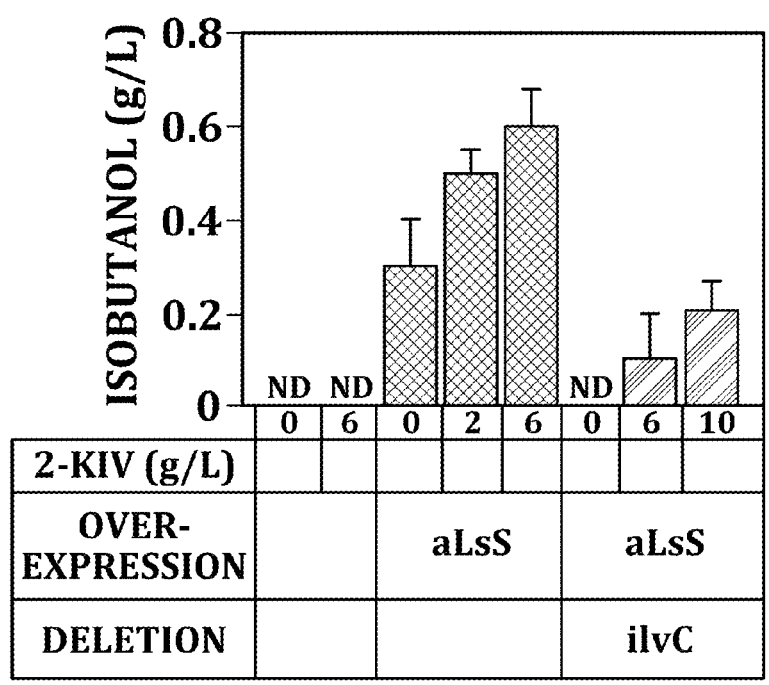
Figure 2C:
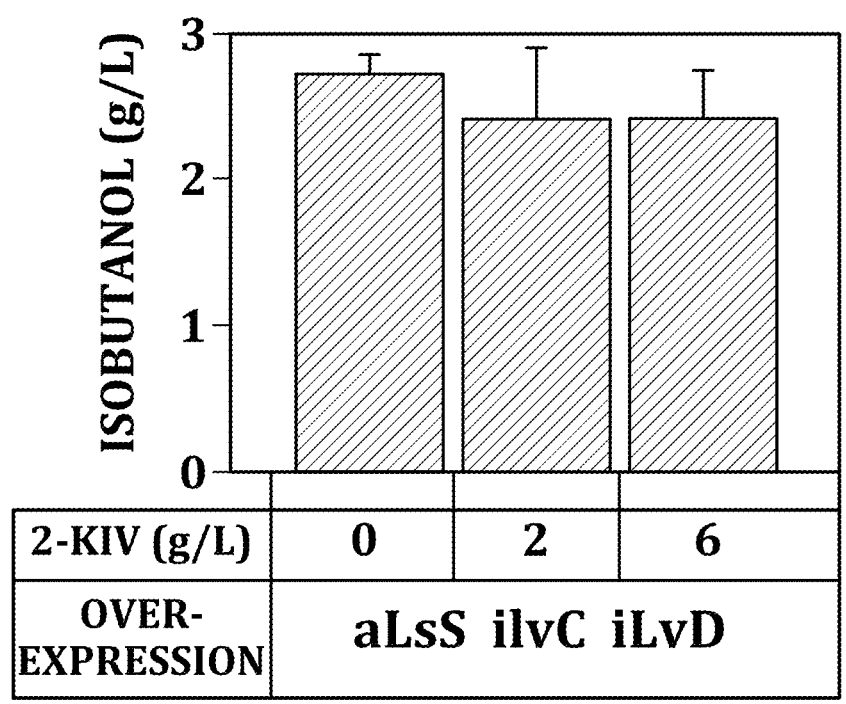

KIV was then supplied to the medium to assess the capability to utilize KIV for isobutanol production (FIG. 2B). The strain without AlsS did not produce isobutanol in the presence of 6 g/liter of KIV (FIG. 2B), but addition of KIV to strains over-expressing alsS led to isobutanol production in the wild-type and ΔilvC backgrounds (FIG. 2B). These tests revealed that Kdc-independent isobutanol production requires over-expression of alsS and a high concentration of KIV. Feeding of KIV to the strain over-expressing alsS, ilvC, and ilvD did not change the production of isobutanol (FIG. 2C), presumably because the concentration of KIV may already saturate the enzyme which utilizes KIV for isobutanol production or the efficiency of KIV uptake may decrease (FIG. 2C).

Characterization of wild type and AlsS variants. It was hypothesized that AlsS could catalyze the decarboxylation of KIV and give isobutyraldehyde without the nucleophilic attack of the second pyruvate in the presence of a high concentration of KIV and a low concentration of pyruvate. Because the over-expression of alsS, ilvC, and ilvD significantly decreases the secretion of pyruvate to below a detection limit of 0.1 mM (the host strain without these plasmids secretes 7 mM pyruvate), it is possible that under this condition, KIV reacts with TPP and undergoes decarboxylation, and then escapes by giving isobutyraldehyde before undergoing the carboligation.

Figure 3A:
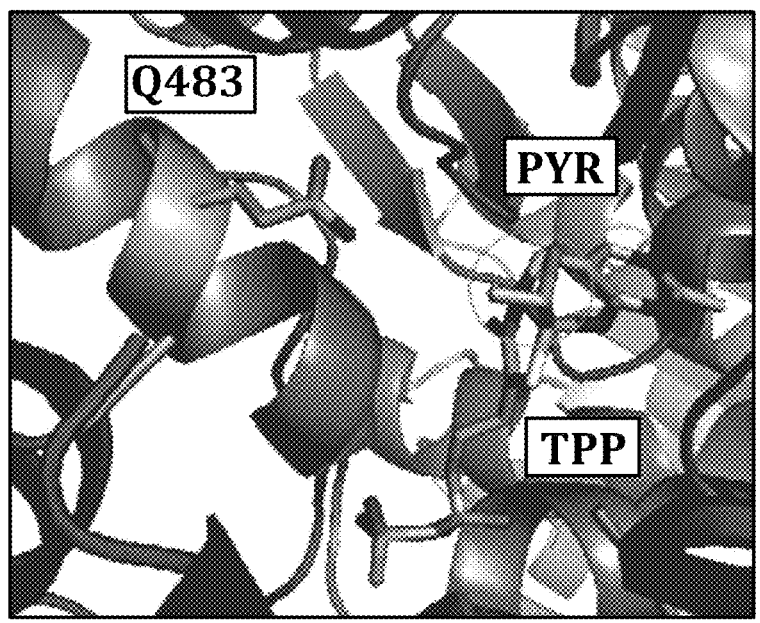
FIG. 3A shows the active site region of *K. pneumoniae* AlsS. Q483 and TPP reacted with the first pyruvate are marked.
Figure 3B:
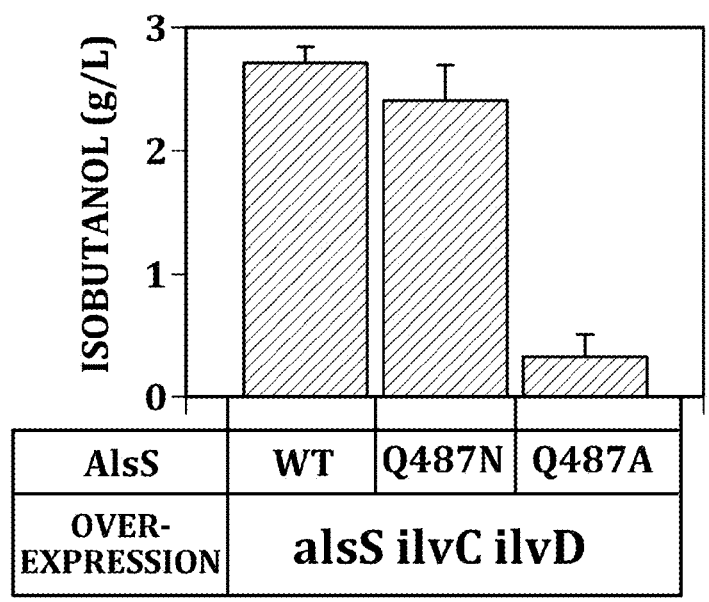
FIGS. 3B and 3C: Isobutanol production with the AlsS mutants.
Figure 3C:
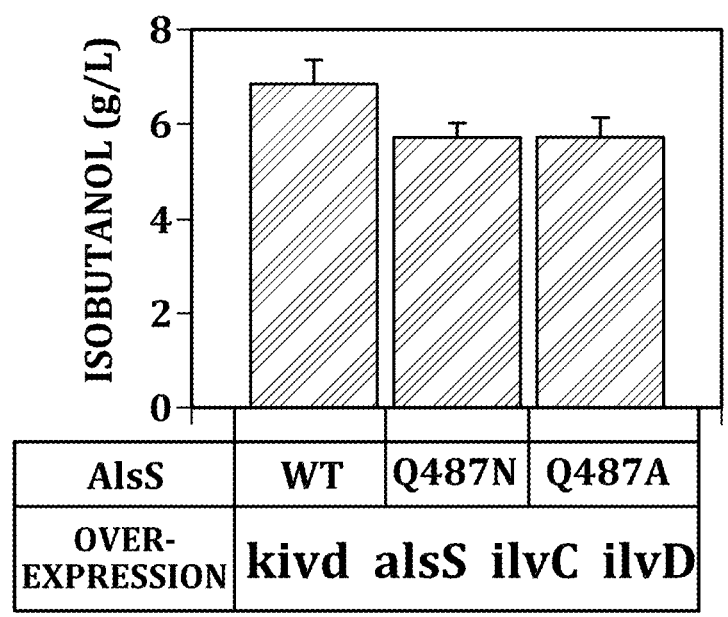

Purification and characterization of wild type and AlsS variants. Using the crystal structure of Klebsiella pneumoniae AlsS, Pang et al., (2004) J. Biol. Chem. 279:2242-2253) showed that the extended side chain of Gln483 causes steric hindrance with the larger substrate, 2-ketobutyrate, which explains why AlsS reacts very poorly with a larger 2-keto acid as the second substrate (Gollop et al., (1990) J. Bacteriol. 172:344-3449; Pang et al., (2004) J. Biol. Chem. 279:2242-2253). Gln483 in K. pneumoniae AlsS has been shown to be in close proximity to the first pyruvate and also involved in second-substrate specificity (Pang et al., (2004) J. Biol. Chem. 279:2242-2253), suggesting that Gln483 may play a role in the release of aldehydes (see FIG. 3A). The residue corresponding to Gln483 in K. pneumoniae AlsS is Gln487 in B. subtilis AlsS. To test whether Gln487 could play a role in decarboxylation, Gln487 was replaced with various other amino acids. For example, Gln487 was replaced with Asn and Ala. The side-chain of Asn has an amine group like Gln but it is shorter than that of Gln. The side-chain of Ala is shorter than that of Gln but does not contain an amine group. These AlsS mutants were over-expressed with INC and IlvD. Isobutanol production with AlsS (Q487N) and AlsS (Q487A) decreased by 25% and 90%, respectively (FIG. 3B). The replacement of Q487 with alanine nearly abolished isobutanol production, indicating that this residue is important for either acetolactate synthase or 2-ketoisovalerate decarboxylase activity. To test which reactions were affected by these mutations, KDC was over-expressed (FIG. 3C). With over-expression of KDC, all strains produced similar levels of isobutanol (FIG. 3C), indicating the replacement of Q487 only affected the decarboxylase activity.

Purification and characterization of wild type and AlsS variants. To assay the Kdc activity (FIG. 1C, bottom) of AlsS, His-tagged wild-type AlsS was expressed from a His-tag plasmid and purified as described above. The Kdc activity of the His-tagged wild-type AlsS was 5.5 µmol·min$^{-1}$·mg$^{-1}$, while isobutyraldehyde production was not detected from a negative control experiment without AlsS. Although the activity was weak, AlsS showed the decarboxylase activity toward KIV in vitro.

The kinetic parameters were measured for AlsS variants (Table 2). The $k_{cat}/K_m$ values for pyruvate of Q487 variants with small residues (Q487A, Q487G, and Q487S) were similar to that of the wild type, while the $k_{cat}/K_m$ values for KIV of these variants decreased dramatically (Table 2). Q487L and Q487I replacements impaired Als activity (Table 2). However, the $k_{cat}/K_m$ values for KIV of these variants were similar to that of the wild type. The wild type and all variants showed extremely high $K_m$ values for KIV (Table 2), which may explain why an increase of the flux toward KIV is required for the decarboxylase activity of AlsS.

Figure 4A:
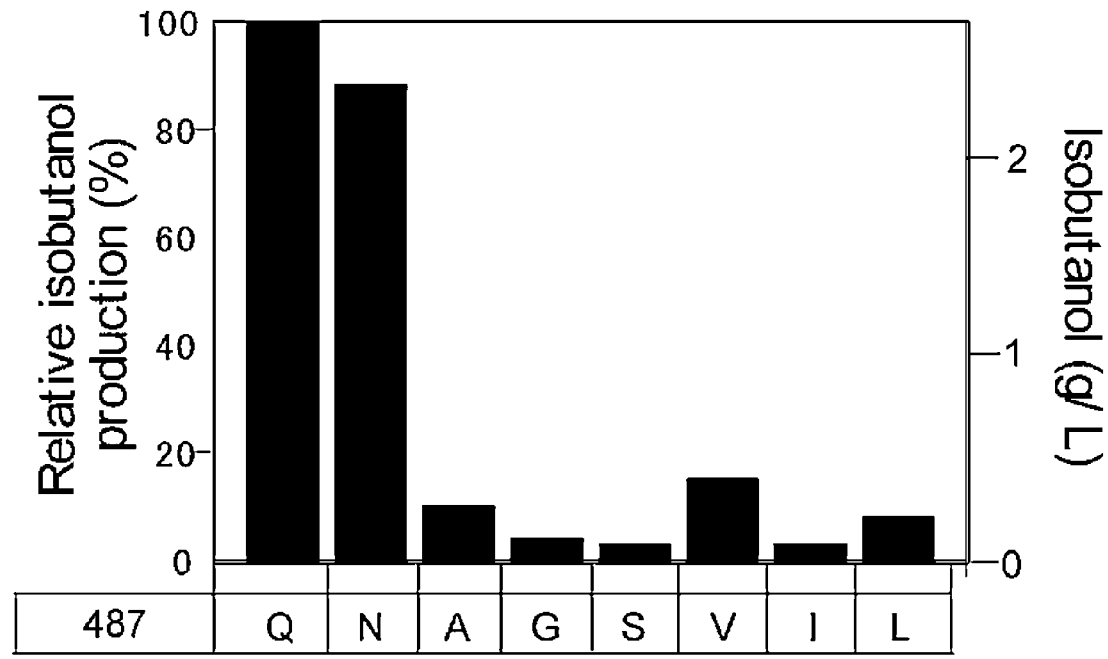
FIGS. 4A-4C show the effect of Q487 on the decarboxylase activity of AlsS.

Effects of Q487 replacements for isobutanol production. To test these AlsS variants' capability to produce isobutanol, which requires both Als (FIG. 1C, top) and Kdc (FIG. 1C, bottom) activities, these alsS variants were over-expressed with ilvC and ilvD. Isobutanol production with AlsS (Q487N) was similar to the production achieved using wild-type AlsS (FIG. 4A), presumably because the side chain of Asn has an amine group, like Gln. However, the replacement of Q487 with valine, alanine, glycine, serine, leucine, and isoleucine nearly abolished isobutanol production (FIG. 4A). According to the results of the performed enzyme assays (Table 2), the replacement of Q487 with glycine and serine maintained Als activity and decreased Kdc activity. The ratios of $K_m$ for KIV to $K_m$ for pyruvate of Q487G and Q487S were 109±30 and 140±79, respectively, while the ratio for the wild-type enzyme was 20±2.9. The strains with either Q487G or Q487S cannot produce isobutanol, presumably because the Kdc activity of Q487G and Q487S could not compete with the Als activity. Enzyme assays showed that Q487L and Q487I replacements impaired Als activity. Increased flux toward KIV was found to be important for isobutanol production when using AlsS for Kdc activity (FIGS. 2A and 2B), but the $K_m$ values for KIV of Q487L and Q487I were 342±45 mM and 323±26 mM, respectively (Table 2), which were extremely high. Because these $K_m$ values are extremely high, the strains with these replacements could not produce isobutanol, presumably because the intracellular concentration of KIV would not be high enough for the Kdc activity. No replacements were found that could increase isobutanol production.

Figure 4B:
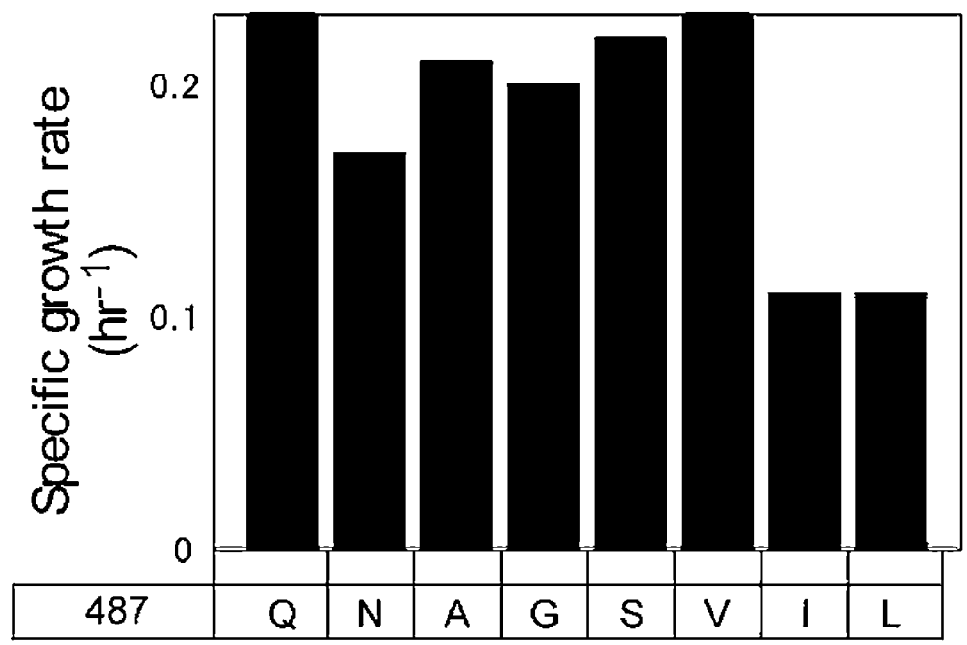

Effects of Q487 replacements for Als activity. To distinguish between Als and Kdc activities in these variants, the growth rate of an *E. coli* strain KS145 (ΔilvI ΔilvB) expressing various Q487 variants was tested in a minimum glucose medium supplemented with L-isoleucine. AlsS is a distant homologue of Ahas, which is responsible for both Als (FIG. 1C, top) and 2-aceto-2-hydroxy butyrate synthase (Ahbs) (FIG. 1C, middle) activities in the branched chain amino acid biosynthesis. The KS145 strain does not have Als and Ahbs activities (FIG. 1C); thus, the specific growth rate in the minimal medium with L-isoleucine reflects the Als activity. FIG. 4B shows that all of the Q487 variants retain significant Als activity. Considering that most of the Q487 variants did not generate isobutanol (FIG. 4A), it was concluded that AlsS is indeed responsible for the Kdc activity observed in isobutanol synthesis, and that Q487 is important for this activity. KS145 cells expressing Q487L or Q487I showed slow growth with the L-isoleucine supplement (FIG. 4B), indicating that these replacements would reduce Als activity. These results were consistent with the results of enzyme assays (Table 2). In the structure model of *K. pneumoniae* AlsS, the C-1 carbonyl oxygen of the modeled second pyruvate is hydrogen-bonded to the side chain of Gln483 (Pang et al., (2004) *J. Biol. Chem.* 279:2242-2253). Thus, the nonpolar side chain of isoleucine and leucine in the 487th residue would reduce the binding affinity of the second pyruvate to the site. No growth phenotype was observed in any strain while grown on minimum glucose medium supplemented with L-valine, L-leucine, and L-isoleucine.

Figure 1C:
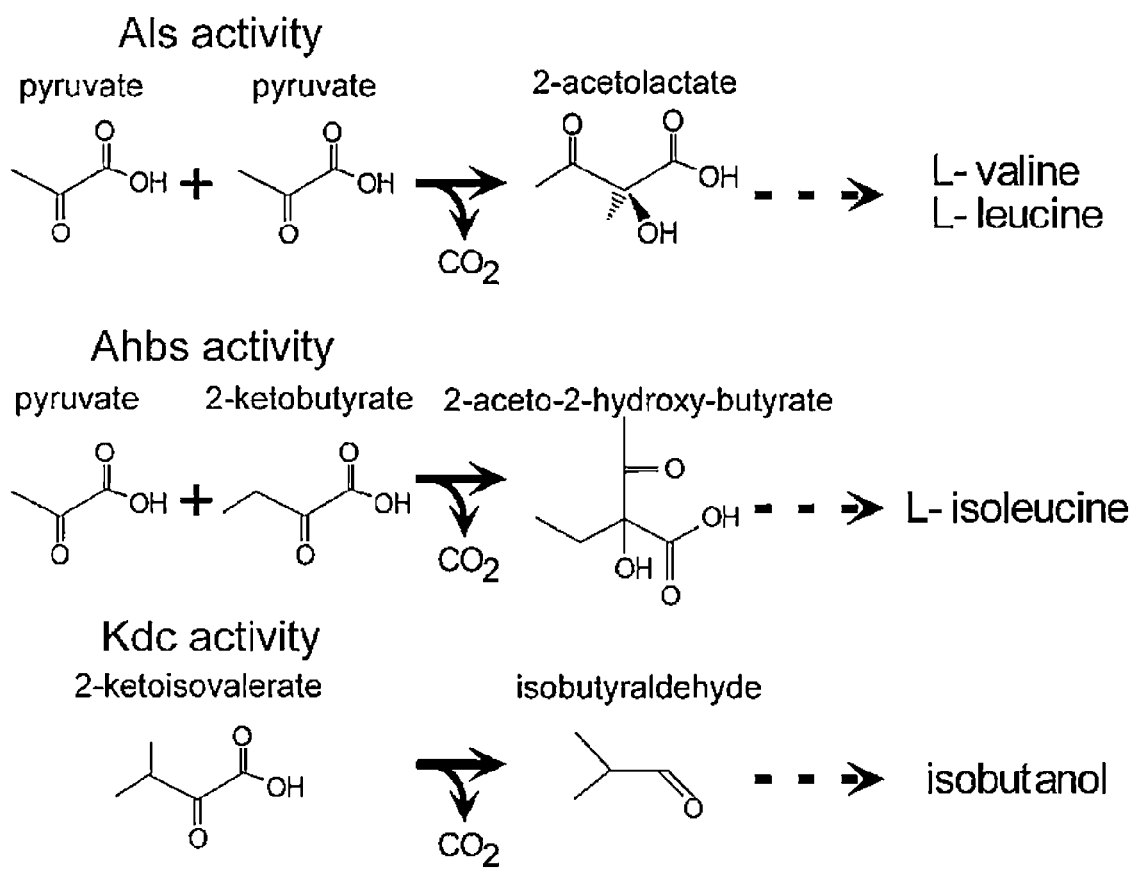
FIG. 1C: Enzymatic reaction of Als, Ahbs, and Kdc activities.
Figure 4C:
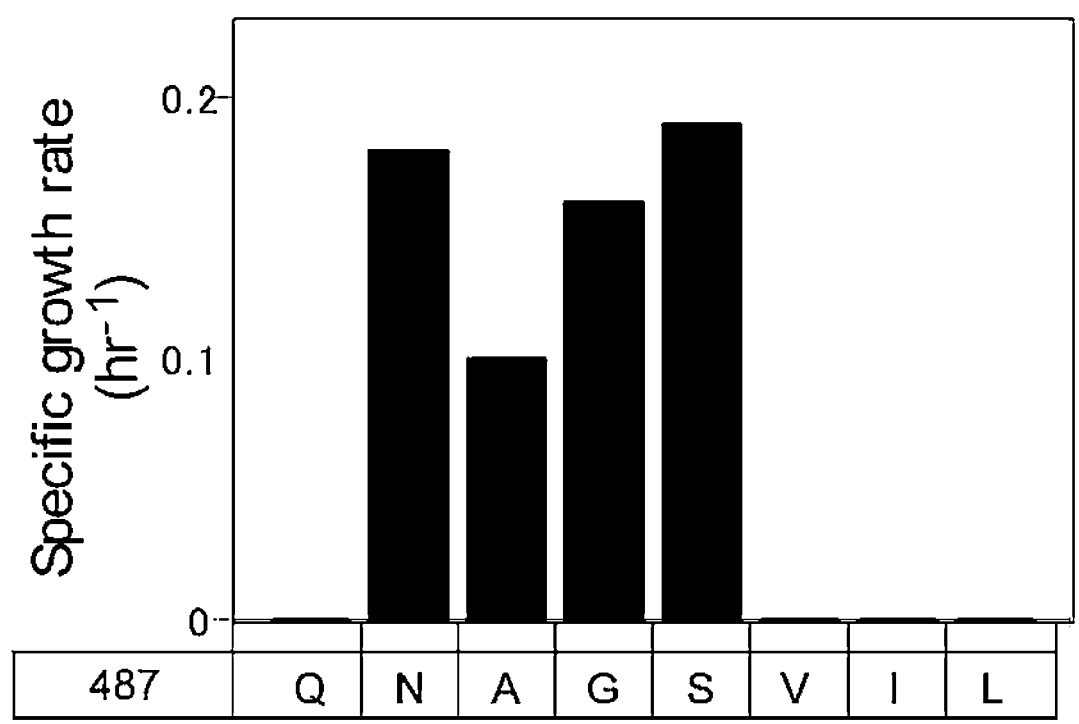

Effects of Q487 replacements for Ahbs activity. AlsS reacts very poorly with the larger substrate, 2-ketobutyrate (Gollop et al., (1990) *J. Bacteriol.* 172:3444-3449). If these replacements change the second substrate specificity by removing steric hindrance, the AlsS variants would gain the Ahbs activity so that the KS145 cells expressing the variants could grow in minimal medium with L-valine and L-leucine supplementation. As predicted, KS145 cells expressing the wild-type AlsS were unable to grow without L-isoleucine (FIG. 4C), indicating that the wild-type AlsS was not capable of catalyzing Ahbs reaction, which is consistent with previous studies (Huseby and Stormer, (1971) *Eur. J. Biochem.* 20:215-217). Interestingly, the AlsS variants which contain small residues (Ala, Gly, and Ser) at the 487th residue rescued the growth of KS145 under the same conditions (FIG. 4C). This result suggests that the replacement of Q487 with small side chain amino acids would make the substrate binding site larger so that the variants are able to react with 2-ketobutyrate as the second substrate (Ahbs activity) (FIG. 1C, middle).

The foregoing evidence shows that Kdc is not essential for isobutanol production and that AlsS, previously known only to have Als activity, can catalyze the decarboxylation of KIV. The use of mutational studies allowed the inventors to identify that Q487 is important for Kdc activity. The disclosure also demonstrates that AlsS is able to function as a KDC to release aldehydes after decarboxylation. KDC requires only one substrate binding event and one catalytic reaction, while ALS requires two substrate binding events and two catalytic reactions (decarboxylation and ligation using the second substrate). Since KDC is simpler than ALS, KDC may have arisen earlier than ALS.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

The embodiments of the invention in which an exclusive property or privilege is claimed are defined as follow:

1. A recombinant bacterium that produces isobutanol, wherein the isobutanol is produced from a 2-ketoisovalerate intermediate, wherein the recombinant bacterium lacks a gene encoding a 2-ketoacid decarboxylase, wherein the recombinant bacterium expresses a heterologous acetolactate synthase having an amino acid sequence with 80% identity to the sequence of SEQ ID NO:2 or SEQ ID NO:7 and having decarboxylase activity to convert the 2-ketoisovalerate intermediate to an isobutyraldehyde intermediate.

2. The recombinant bacterium of claim 1, wherein the acetolactate synthase is from *Bacillus subtilis*.

3. The recombinant bacterium of claim 2, wherein the acetolactate synthase comprises SEQ ID NO:2.

4. The recombinant bacterium of claim 2, wherein the acetolactate synthase comprises SEQ ID NO:7.

5. The recombinant bacterium of claim 1, wherein the bacterium is an *Escherichia coli*.

6. The recombinant bacterium of claim 1, wherein the microorganism is from a genus of *Escherichia, Lactobacillus, Bacillus, Lactococcus, Salmonella, Enterobacter, Enterococcus, Erwinia, Pantoea, Morganella, Pectobacterium, Proteus, Serratia, Shigella, Klebsiella*, or *Citrobacter*.

7. A method for producing isobutanol, the method comprising:
(a) viding a recombinant bacterium of claim 1;
(b) culturing the bacterium of (a) in the presence of a suitable substrate or metabolic intermediate and under conditions suitable for the conversion of the substrate or metabolic intermediate to isobutanol; and
(c) substantially purifying the isobutanol.

* * * * *

SEQUENCE LISTING

```
<160> NUMBER OF SEQ ID NOS: 17

<210> SEQ ID NO 1
<211> LENGTH: 1716
<212> TYPE: DNA
<213> ORGANISM: Bacillus subtilis
<220> FEATURE:
<221> NAME/KEY: CDS
<222> LOCATION: (1)..(1716)

<400> SEQUENCE: 1 gtg ttg aca aaa gca aca aaa gaa caa aaa tcc ctt gtg aaa aac aga        48
Val Leu Thr Lys Ala Thr Lys Glu Gln Lys Ser Leu Val Lys Asn Arg
1               5                   10                  15 ggg gcg gag ctt gtt gtt gat tgc tta gtg gag caa ggt gtc aca cat        96
Gly Ala Glu Leu Val Val Asp Cys Leu Val Glu Gln Gly Val Thr His
            20                  25                  30 gta ttt ggc att cca ggt gca aaa att gat gcg gta ttt gac gct tta       144
Val Phe Gly Ile Pro Gly Ala Lys Ile Asp Ala Val Phe Asp Ala Leu
        35                  40                  45
```

| | | |
|---|---|---|
| caa gat aaa gga cct gaa att atc gtt gcc cgg cac gaa caa aac gca<br>Gln Asp Lys Gly Pro Glu Ile Ile Val Ala Arg His Glu Gln Asn Ala<br>50 55 60 | | 192 |
| gca ttc atg gcc caa gca gtc ggc cgt tta act gga aaa ccg gga gtc<br>Ala Phe Met Ala Gln Ala Val Gly Arg Leu Thr Gly Lys Pro Gly Val<br>65 70 75 80 | | 240 |
| gtg tta gtc aca tca gga ccg ggt gcc tct aac ttg gca aca ggc ctg<br>Val Leu Val Thr Ser Gly Pro Gly Ala Ser Asn Leu Ala Thr Gly Leu<br>85 90 95 | | 288 |
| ctg aca gcg aac act gaa gga gac cct gtc gtt gcg ctt gct gga aac<br>Leu Thr Ala Asn Thr Glu Gly Asp Pro Val Val Ala Leu Ala Gly Asn<br>100 105 110 | | 336 |
| gtg atc cgt gca gat cgt tta aaa cgg aca cat caa tct ttg gat aat<br>Val Ile Arg Ala Asp Arg Leu Lys Arg Thr His Gln Ser Leu Asp Asn<br>115 120 125 | | 384 |
| gcg gcg cta ttc cag ccg att aca aaa tac agt gta gaa gtt caa gat<br>Ala Ala Leu Phe Gln Pro Ile Thr Lys Tyr Ser Val Glu Val Gln Asp<br>130 135 140 | | 432 |
| gta aaa aat ata ccg gaa gct gtt aca aat gca ttt agg ata gcg tca<br>Val Lys Asn Ile Pro Glu Ala Val Thr Asn Ala Phe Arg Ile Ala Ser<br>145 150 155 160 | | 480 |
| gca ggg cag gct ggg gcc gct ttt gtg agc ttt ccg caa gat gtt gtg<br>Ala Gly Gln Ala Gly Ala Ala Phe Val Ser Phe Pro Gln Asp Val Val<br>165 170 175 | | 528 |
| aat gaa gtc aca aat acg aaa aac gtg cgt gct gtt gca gcg cca aaa<br>Asn Glu Val Thr Asn Thr Lys Asn Val Arg Ala Val Ala Ala Pro Lys<br>180 185 190 | | 576 |
| ctc ggt cct gca gca gat gat gca atc agt gcg gcc ata gca aaa atc<br>Leu Gly Pro Ala Ala Asp Asp Ala Ile Ser Ala Ala Ile Ala Lys Ile<br>195 200 205 | | 624 |
| caa aca gca aaa ctt cct gtc gtt ttg gtc ggc atg aaa ggc gga aga<br>Gln Thr Ala Lys Leu Pro Val Val Leu Val Gly Met Lys Gly Gly Arg<br>210 215 220 | | 672 |
| ccg gaa gca att aaa gcg gtt cgc aag ctt ttg aaa aag gtt cag ctt<br>Pro Glu Ala Ile Lys Ala Val Arg Lys Leu Leu Lys Lys Val Gln Leu<br>225 230 235 240 | | 720 |
| cca ttt gtt gaa aca tat caa gct gcc ggt acc ctt tct aga gat tta<br>Pro Phe Val Glu Thr Tyr Gln Ala Ala Gly Thr Leu Ser Arg Asp Leu<br>245 250 255 | | 768 |
| gag gat caa tat ttt ggc cgt atc ggt ttg ttc cgc aac cag cct ggc<br>Glu Asp Gln Tyr Phe Gly Arg Ile Gly Leu Phe Arg Asn Gln Pro Gly<br>260 265 270 | | 816 |
| gat tta ctg cta gag cag gca gat gtt gtt ctg acg atc ggc tat gac<br>Asp Leu Leu Leu Glu Gln Ala Asp Val Val Leu Thr Ile Gly Tyr Asp<br>275 280 285 | | 864 |
| ccg att gaa tat gat ccg aaa ttc tgg aat atc aat gga gac cgg aca<br>Pro Ile Glu Tyr Asp Pro Lys Phe Trp Asn Ile Asn Gly Asp Arg Thr<br>290 295 300 | | 912 |
| att atc cat tta gac gag att atc gct gac att gat cat gct tac cag<br>Ile Ile His Leu Asp Glu Ile Ile Ala Asp Ile Asp His Ala Tyr Gln<br>305 310 315 320 | | 960 |
| cct gat ctt gaa ttg atc ggt gac att ccg tcc acg atc aat cat atc<br>Pro Asp Leu Glu Leu Ile Gly Asp Ile Pro Ser Thr Ile Asn His Ile<br>325 330 335 | | 1008 |
| gaa cac gat gct gtg aaa gtg gaa ttt gca gag cgt gag cag aaa atc<br>Glu His Asp Ala Val Lys Val Glu Phe Ala Glu Arg Glu Gln Lys Ile<br>340 345 350 | | 1056 |
| ctt tct gat tta aaa caa tat atg cat gaa ggt gag cag gtg cct gca<br>Leu Ser Asp Leu Lys Gln Tyr Met His Glu Gly Glu Gln Val Pro Ala<br>355 360 365 | | 1104 |

```
gat tgg aaa tca gac aga gcg cac cct ctt gaa atc gtt aaa gag ttg      1152
Asp Trp Lys Ser Asp Arg Ala His Pro Leu Glu Ile Val Lys Glu Leu
    370             375                 380 cgt aat gca gtc gat gat cat gtt aca gta act tgc gat atc ggt tcg      1200
Arg Asn Ala Val Asp Asp His Val Thr Val Thr Cys Asp Ile Gly Ser
385                 390                 395                 400 cac gcc att tgg atg tca cgt tat ttc cgc agc tac gag ccg tta aca      1248
His Ala Ile Trp Met Ser Arg Tyr Phe Arg Ser Tyr Glu Pro Leu Thr
                405                 410                 415 tta atg atc agt aac ggt atg caa aca ctc ggc gtt gcg ctt cct tgg      1296
Leu Met Ile Ser Asn Gly Met Gln Thr Leu Gly Val Ala Leu Pro Trp
            420                 425                 430 gca atc ggc gct tca ttg gtg aaa ccg gga gaa aaa gtg gtt tct gtc      1344
Ala Ile Gly Ala Ser Leu Val Lys Pro Gly Glu Lys Val Val Ser Val
        435                 440                 445 tct ggt gac ggc ggt ttc tta ttc tca gca atg gaa tta gag aca gca      1392
Ser Gly Asp Gly Gly Phe Leu Phe Ser Ala Met Glu Leu Glu Thr Ala
450                 455                 460 gtt cga cta aaa gca cca att gta cac att gta tgg aac gac agc aca      1440
Val Arg Leu Lys Ala Pro Ile Val His Ile Val Trp Asn Asp Ser Thr
465                 470                 475                 480 tat gac atg gtt gca ttc cag caa ttg aaa aaa tat aac cgt aca tct      1488
Tyr Asp Met Val Ala Phe Gln Gln Leu Lys Lys Tyr Asn Arg Thr Ser
                485                 490                 495 gcg gtc gat ttc gga aat atc gat atc gtg aaa tat gcg gaa agc ttc      1536
Ala Val Asp Phe Gly Asn Ile Asp Ile Val Lys Tyr Ala Glu Ser Phe
            500                 505                 510 gga gca act ggc ttg cgc gta gaa tca cca gac cag ctg gca gat gtt      1584
Gly Ala Thr Gly Leu Arg Val Glu Ser Pro Asp Gln Leu Ala Asp Val
        515                 520                 525 ctg cgt caa ggc atg aac gct gaa ggt cct gtc atc atc gat gtc ccg      1632
Leu Arg Gln Gly Met Asn Ala Glu Gly Pro Val Ile Ile Asp Val Pro
530                 535                 540 gtt gac tac agt gat aac att aat tta gca agt gac aag ctt ccg aaa      1680
Val Asp Tyr Ser Asp Asn Ile Asn Leu Ala Ser Asp Lys Leu Pro Lys
545                 550                 555                 560 gaa ttc ggg gaa ctc atg aaa acg aaa gct ctc tag                      1716
Glu Phe Gly Glu Leu Met Lys Thr Lys Ala Leu
                565                 570

<210> SEQ ID NO 2
<211> LENGTH: 571
<212> TYPE: PRT
<213> ORGANISM: Bacillus subtilis

<400> SEQUENCE: 2

Val Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95
```

```
Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510
```

-continued

```
Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 3
<211> LENGTH: 1716
<212> TYPE: DNA
<213> ORGANISM: Artificial sequence
<220> FEATURE:
<223> OTHER INFORMATION: Synthetic
<220> FEATURE:
<221> NAME/KEY: CDS
<222> LOCATION: (1)..(1716)

<400> SEQUENCE: 3
```

| | | | | | | | | | | | | | | | | |
|---|---|---|---|---|---|---|---|---|---|---|---|---|---|---|---|---|
| atg | ttg | aca | aaa | gca | aca | aaa | gaa | caa | aaa | tcc | ctt | gtg | aaa | aac | aga | 48 |
| Met | Leu | Thr | Lys | Ala | Thr | Lys | Glu | Gln | Lys | Ser | Leu | Val | Lys | Asn | Arg | |
| 1 | | | | 5 | | | | | 10 | | | | | 15 | | |
| ggg | gcg | gag | ctt | gtt | gtt | gat | tgc | tta | gtg | gag | caa | ggt | gtc | aca | cat | 96 |
| Gly | Ala | Glu | Leu | Val | Val | Asp | Cys | Leu | Val | Glu | Gln | Gly | Val | Thr | His | |
| | | | 20 | | | | | 25 | | | | | 30 | | | |
| gta | ttt | ggc | att | cca | ggt | gca | aaa | att | gat | gcg | gta | ttt | gac | gct | tta | 144 |
| Val | Phe | Gly | Ile | Pro | Gly | Ala | Lys | Ile | Asp | Ala | Val | Phe | Asp | Ala | Leu | |
| | | 35 | | | | | 40 | | | | | 45 | | | | |
| caa | gat | aaa | gga | cct | gaa | att | atc | gtt | gcc | cgg | cac | gaa | caa | aac | gca | 192 |
| Gln | Asp | Lys | Gly | Pro | Glu | Ile | Ile | Val | Ala | Arg | His | Glu | Gln | Asn | Ala | |
| 50 | | | | | 55 | | | | | 60 | | | | | | |
| gca | ttc | atg | gcc | caa | gca | gtc | ggc | cgt | tta | act | gga | aaa | ccg | gga | gtc | 240 |
| Ala | Phe | Met | Ala | Gln | Ala | Val | Gly | Arg | Leu | Thr | Gly | Lys | Pro | Gly | Val | |
| 65 | | | | | 70 | | | | | 75 | | | | | 80 | |
| gtg | tta | gtc | aca | tca | gga | ccg | ggt | gcc | tct | aac | ttg | gca | aca | ggc | ctg | 288 |
| Val | Leu | Val | Thr | Ser | Gly | Pro | Gly | Ala | Ser | Asn | Leu | Ala | Thr | Gly | Leu | |
| | | | | 85 | | | | | 90 | | | | | 95 | | |
| ctg | aca | gcg | aac | act | gaa | gga | gac | cct | gtc | gtt | gcg | ctt | gct | gga | aac | 336 |
| Leu | Thr | Ala | Asn | Thr | Glu | Gly | Asp | Pro | Val | Val | Ala | Leu | Ala | Gly | Asn | |
| | | | 100 | | | | | 105 | | | | | 110 | | | |
| gtg | atc | cgt | gca | gat | cgt | tta | aaa | cgg | aca | cat | caa | tct | ttg | gat | aat | 384 |
| Val | Ile | Arg | Ala | Asp | Arg | Leu | Lys | Arg | Thr | His | Gln | Ser | Leu | Asp | Asn | |
| | | 115 | | | | | 120 | | | | | 125 | | | | |
| gcg | gcg | cta | ttc | cag | ccg | att | aca | aaa | tac | agt | gta | gaa | gtt | caa | gat | 432 |
| Ala | Ala | Leu | Phe | Gln | Pro | Ile | Thr | Lys | Tyr | Ser | Val | Glu | Val | Gln | Asp | |
| | 130 | | | | | 135 | | | | | 140 | | | | | |
| gta | aaa | aat | ata | ccg | gaa | gct | gtt | aca | aat | gca | ttt | agg | ata | gcg | tca | 480 |
| Val | Lys | Asn | Ile | Pro | Glu | Ala | Val | Thr | Asn | Ala | Phe | Arg | Ile | Ala | Ser | |
| 145 | | | | | 150 | | | | | 155 | | | | | 160 | |
| gca | ggg | cag | gct | ggg | gcc | gct | ttt | gtg | agc | ttt | ccg | caa | gat | gtt | gtg | 528 |
| Ala | Gly | Gln | Ala | Gly | Ala | Ala | Phe | Val | Ser | Phe | Pro | Gln | Asp | Val | Val | |
| | | | | 165 | | | | | 170 | | | | | 175 | | |
| aat | gaa | gtc | aca | aat | acg | aaa | aac | gtg | cgt | gct | gtt | gca | gcg | cca | aaa | 576 |
| Asn | Glu | Val | Thr | Asn | Thr | Lys | Asn | Val | Arg | Ala | Val | Ala | Ala | Pro | Lys | |
| | | | 180 | | | | | 185 | | | | | 190 | | | |
| ctc | ggt | cct | gca | gca | gat | gat | gca | atc | agt | gcg | gcc | ata | gca | aaa | atc | 624 |
| Leu | Gly | Pro | Ala | Ala | Asp | Asp | Ala | Ile | Ser | Ala | Ala | Ile | Ala | Lys | Ile | |
| | | 195 | | | | | 200 | | | | | 205 | | | | |

| | |
|---|---|
| caa aca gca aaa ctt cct gtc gtt ttg gtc ggc atg aaa ggc gga aga<br>Gln Thr Ala Lys Leu Pro Val Val Leu Val Gly Met Lys Gly Gly Arg<br>    210                       215                    220 | 672 |
| ccg gaa gca att aaa gcg gtt cgc aag ctt ttg aaa aag gtt cag ctt<br>Pro Glu Ala Ile Lys Ala Val Arg Lys Leu Leu Lys Lys Val Gln Leu<br>225                       230                     235                  240 | 720 |
| cca ttt gtt gaa aca tat caa gct gcc ggt acc ctt tct aga gat tta<br>Pro Phe Val Glu Thr Tyr Gln Ala Ala Gly Thr Leu Ser Arg Asp Leu<br>                    245                    250                    255 | 768 |
| gag gat caa tat ttt ggc cgt atc ggt ttg ttc cgc aac cag cct ggc<br>Glu Asp Gln Tyr Phe Gly Arg Ile Gly Leu Phe Arg Asn Gln Pro Gly<br>         260                     265                    270 | 816 |
| gat tta ctg cta gag cag gca gat gtt gtt ctg acg atc ggc tat gac<br>Asp Leu Leu Leu Glu Gln Ala Asp Val Val Leu Thr Ile Gly Tyr Asp<br>    275                     280                    285 | 864 |
| ccg att gaa tat gat ccg aaa ttc tgg aat atc aat gga gac cgg aca<br>Pro Ile Glu Tyr Asp Pro Lys Phe Trp Asn Ile Asn Gly Asp Arg Thr<br>290                     295                    300 | 912 |
| att atc cat tta gac gag att atc gct gac att gat cat gct tac cag<br>Ile Ile His Leu Asp Glu Ile Ile Ala Asp Ile Asp His Ala Tyr Gln<br>305                     310                    315                  320 | 960 |
| cct gat ctt gaa ttg atc ggt gac att ccg tcc acg atc aat cat atc<br>Pro Asp Leu Glu Leu Ile Gly Asp Ile Pro Ser Thr Ile Asn His Ile<br>                    325                    330                    335 | 1008 |
| gaa cac gat gct gtg aaa gtg gaa ttt gca gag cgt gag cag aaa atc<br>Glu His Asp Ala Val Lys Val Glu Phe Ala Glu Arg Glu Gln Lys Ile<br>                  340                    345                    350 | 1056 |
| ctt tct gat tta aaa caa tat atg cat gaa ggt gag cag gtg cct gca<br>Leu Ser Asp Leu Lys Gln Tyr Met His Glu Gly Glu Gln Val Pro Ala<br>              355                    360                    365 | 1104 |
| gat tgg aaa tca gac aga gcg cac cct ctt gaa atc gtt aaa gag ttg<br>Asp Trp Lys Ser Asp Arg Ala His Pro Leu Glu Ile Val Lys Glu Leu<br>    370                     375                    380 | 1152 |
| cgt aat gca gtc gat gat cat gtt aca gta act tgc gat atc ggt tcg<br>Arg Asn Ala Val Asp Asp His Val Thr Val Thr Cys Asp Ile Gly Ser<br>385                     390                    395                  400 | 1200 |
| cac gcc att tgg atg tca cgt tat ttc cgc agc tac gag ccg tta aca<br>His Ala Ile Trp Met Ser Arg Tyr Phe Arg Ser Tyr Glu Pro Leu Thr<br>                  405                    410                    415 | 1248 |
| tta atg atc agt aac ggt atg caa aca ctc ggc gtt gcg ctt cct tgg<br>Leu Met Ile Ser Asn Gly Met Gln Thr Leu Gly Val Ala Leu Pro Trp<br>              420                    425                    430 | 1296 |
| gca atc ggc gct tca ttg gtg aaa ccg gga gaa aaa gtg gtt tct gtc<br>Ala Ile Gly Ala Ser Leu Val Lys Pro Gly Glu Lys Val Val Ser Val<br>    435                     440                    445 | 1344 |
| tct ggt gac ggc ggt ttc tta ttc tca gca atg gaa tta gag aca gca<br>Ser Gly Asp Gly Gly Phe Leu Phe Ser Ala Met Glu Leu Glu Thr Ala<br>450                     455                    460 | 1392 |
| gtt cga cta aaa gca cca att gta cac att gta tgg aac gac agc aca<br>Val Arg Leu Lys Ala Pro Ile Val His Ile Val Trp Asn Asp Ser Thr<br>465                     470                    475                  480 | 1440 |
| tat gac atg gtt gca ttc cag caa ttg aaa aaa tat aac cgt aca tct<br>Tyr Asp Met Val Ala Phe Gln Gln Leu Lys Lys Tyr Asn Arg Thr Ser<br>                  485                    490                    495 | 1488 |
| gcg gtc gat ttc gga aat atc gat atc gtg aaa tat gcg gaa agc ttc<br>Ala Val Asp Phe Gly Asn Ile Asp Ile Val Lys Tyr Ala Glu Ser Phe<br>              500                    505                    510 | 1536 |
| gga gca act ggc ttg cgc gta gaa tca cca gac cag ctg gca gat gtt<br>Gly Ala Thr Gly Leu Arg Val Glu Ser Pro Asp Gln Leu Ala Asp Val<br>    515                     520                    525 | 1584 |

```
ctg cgt caa ggc atg aac gct gaa ggt cct gtc atc atc gat gtc ccg   1632
Leu Arg Gln Gly Met Asn Ala Glu Gly Pro Val Ile Ile Asp Val Pro
    530             535                 540 gtt gac tac agt gat aac att aat tta gca agt gac aag ctt ccg aaa   1680
Val Asp Tyr Ser Asp Asn Ile Asn Leu Ala Ser Asp Lys Leu Pro Lys
545             550                 555                 560 gaa ttc ggg gaa ctc atg aaa acg aaa gct ctc tag                   1716
Glu Phe Gly Glu Leu Met Lys Thr Lys Ala Leu
                565             570
```

<210> SEQ ID NO 4
<211> LENGTH: 571
<212> TYPE: PRT
<213> ORGANISM: Artificial sequence
<220> FEATURE:
<223> OTHER INFORMATION: Synthetic Construct

<400> SEQUENCE: 4

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65              70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300
```

-continued

```
Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
        340                 345                 350

Leu Ser Asp Leu Lys Gln Tyr Met His Glu Gly Gln Val Pro Ala
    355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

```
<210> SEQ ID NO 5
<211> LENGTH: 1716
<212> TYPE: DNA
<213> ORGANISM: Artificial sequence
<220> FEATURE:
<223> OTHER INFORMATION: Synthetic
<220> FEATURE:
<221> NAME/KEY: CDS
<222> LOCATION: (1)..(1716)

<400> SEQUENCE: 5
```

```
atg ttg aca aaa gca aca aaa gaa caa aaa tcc ctt gtg aaa aac aga     48
Met Leu Thr Lys Ala Thr Lys Glu Gln Lys Ser Leu Val Lys Asn Arg
1               5                   10                  15 ggg gcg gag ctt gtt gtt gat tgc tta gtg gag caa ggt gtc aca cat     96
Gly Ala Glu Leu Val Val Asp Cys Leu Val Glu Gln Gly Val Thr His
            20                  25                  30 gta ttt ggc att cca ggt gca aaa att gat gcg gta ttt gac gct tta    144
Val Phe Gly Ile Pro Gly Ala Lys Ile Asp Ala Val Phe Asp Ala Leu
        35                  40                  45 caa gat aaa gga cct gaa att atc gtt gcc cgg cac gaa caa aac gca    192
Gln Asp Lys Gly Pro Glu Ile Ile Val Ala Arg His Glu Gln Asn Ala
    50                  55                  60
```

```
gca ttc atg gcc caa gca gtc ggc cgt tta act gga aaa ccg gga gtc    240
Ala Phe Met Ala Gln Ala Val Gly Arg Leu Thr Gly Lys Pro Gly Val
 65              70                  75                  80 gtg tta gtc aca tca gga ccg ggt gcc tct aac ttg gca aca ggc ctg    288
Val Leu Val Thr Ser Gly Pro Gly Ala Ser Asn Leu Ala Thr Gly Leu
                 85                  90                  95 ctg aca gcg aac act gaa gga gac cct gtc gtt gcg ctt gct gga aac    336
Leu Thr Ala Asn Thr Glu Gly Asp Pro Val Val Ala Leu Ala Gly Asn
             100                 105                 110 gtg atc cgt gca gat cgt tta aaa cgg aca cat caa tct ttg gat aat    384
Val Ile Arg Ala Asp Arg Leu Lys Arg Thr His Gln Ser Leu Asp Asn
         115                 120                 125 gcg gcg cta ttc cag ccg att aca aaa tac agt gta gaa gtt caa gat    432
Ala Ala Leu Phe Gln Pro Ile Thr Lys Tyr Ser Val Glu Val Gln Asp
     130                 135                 140 gta aaa aat ata ccg gaa gct gtt aca aat gca ttt agg ata gcg tca    480
Val Lys Asn Ile Pro Glu Ala Val Thr Asn Ala Phe Arg Ile Ala Ser
145                 150                 155                 160 gca ggg cag gct ggg gcc gct ttt gtg agc ttt ccg caa gat gtt gtg    528
Ala Gly Gln Ala Gly Ala Ala Phe Val Ser Phe Pro Gln Asp Val Val
                165                 170                 175 aat gaa gtc aca aat acg aaa aac gtg cgt gct gtt gca gcg cca aaa    576
Asn Glu Val Thr Asn Thr Lys Asn Val Arg Ala Val Ala Ala Pro Lys
            180                 185                 190 ctc ggt cct gca gca gat gat gca atc agt gcg gcc ata gca aaa atc    624
Leu Gly Pro Ala Ala Asp Asp Ala Ile Ser Ala Ala Ile Ala Lys Ile
        195                 200                 205 caa aca gca aaa ctt cct gtc gtt ttg gtc ggc atg aaa ggc gga aga    672
Gln Thr Ala Lys Leu Pro Val Val Leu Val Gly Met Lys Gly Gly Arg
    210                 215                 220 ccg gaa gca att aaa gcg gtt cgc aag ctt ttg aaa aag gtt cag ctt    720
Pro Glu Ala Ile Lys Ala Val Arg Lys Leu Leu Lys Lys Val Gln Leu
225                 230                 235                 240 cca ttt gtt gaa aca tat caa gct gcc ggt acc ctt tct aga gat tta    768
Pro Phe Val Glu Thr Tyr Gln Ala Ala Gly Thr Leu Ser Arg Asp Leu
                245                 250                 255 gag gat caa tat ttt ggc cgt atc ggt ttg ttc cgc aac cag cct ggc    816
Glu Asp Gln Tyr Phe Gly Arg Ile Gly Leu Phe Arg Asn Gln Pro Gly
            260                 265                 270 gat tta ctg cta gag cag gca gat gtt gtt ctg acg atc ggc tat gac    864
Asp Leu Leu Leu Glu Gln Ala Asp Val Val Leu Thr Ile Gly Tyr Asp
        275                 280                 285 ccg att gaa tat gat ccg aaa ttc tgg aat atc aat gga gac cgg aca    912
Pro Ile Glu Tyr Asp Pro Lys Phe Trp Asn Ile Asn Gly Asp Arg Thr
    290                 295                 300 att atc cat tta gac gag att atc gct gac att gat cat gct tac cag    960
Ile Ile His Leu Asp Glu Ile Ile Ala Asp Ile Asp His Ala Tyr Gln
305                 310                 315                 320 cct gat ctt gaa ttg atc ggt gac att ccg tcc acg atc aat cat atc   1008
Pro Asp Leu Glu Leu Ile Gly Asp Ile Pro Ser Thr Ile Asn His Ile
                325                 330                 335 gaa cac gat gct gtg aaa gtg gaa ttt gca gag cgt gag cag aaa atc   1056
Glu His Asp Ala Val Lys Val Glu Phe Ala Glu Arg Glu Gln Lys Ile
            340                 345                 350 ctt tct gat tta aaa caa tat atg cat gaa ggt gag cag gtg cct gca   1104
Leu Ser Asp Leu Lys Gln Tyr Met His Glu Gly Glu Gln Val Pro Ala
        355                 360                 365 gat tgg aaa tca gac aga gcg cac cct ctt gaa atc gtt aaa gag ttg   1152
Asp Trp Lys Ser Asp Arg Ala His Pro Leu Glu Ile Val Lys Glu Leu
    370                 375                 380
```

```
cgt aat gca gtc gat gat cat gtt aca gta act tgc gat atc ggt tcg      1200
Arg Asn Ala Val Asp Asp His Val Thr Val Thr Cys Asp Ile Gly Ser
385                 390                 395                 400 cac gcc att tgg atg tca cgt tat ttc cgc agc tac gag ccg tta aca      1248
His Ala Ile Trp Met Ser Arg Tyr Phe Arg Ser Tyr Glu Pro Leu Thr
            405                 410                 415 tta atg atc agt aac ggt atg caa aca ctc ggc gtt gcg ctt cct tgg      1296
Leu Met Ile Ser Asn Gly Met Gln Thr Leu Gly Val Ala Leu Pro Trp
        420                 425                 430 gca atc ggc gct tca ttg gtg aaa ccg gga gaa aaa gtg gtt tct gtc      1344
Ala Ile Gly Ala Ser Leu Val Lys Pro Gly Glu Lys Val Val Ser Val
    435                 440                 445 tct ggt gac ggc ggt ttc tta ttc tca gca atg gaa tta gag aca gca      1392
Ser Gly Asp Gly Gly Phe Leu Phe Ser Ala Met Glu Leu Glu Thr Ala
450                 455                 460 gtt cga cta aaa gca cca att gta cac att gta tgg aac gac agc aca      1440
Val Arg Leu Lys Ala Pro Ile Val His Ile Val Trp Asn Asp Ser Thr
465                 470                 475                 480 tat gac atg gtt gca ttc aac caa ttg aaa aaa tat aac cgt aca tct      1488
Tyr Asp Met Val Ala Phe Asn Gln Leu Lys Lys Tyr Asn Arg Thr Ser
            485                 490                 495 gcg gtc gat ttc gga aat atc gat atc gtg aaa tat gcg gaa agc ttc      1536
Ala Val Asp Phe Gly Asn Ile Asp Ile Val Lys Tyr Ala Glu Ser Phe
        500                 505                 510 gga gca act ggc ttg cgc gta gaa tca cca gac cag ctg gca gat gtt      1584
Gly Ala Thr Gly Leu Arg Val Glu Ser Pro Asp Gln Leu Ala Asp Val
    515                 520                 525 ctg cgt caa ggc atg aac gct gaa ggt cct gtc atc atc gat gtc ccg      1632
Leu Arg Gln Gly Met Asn Ala Glu Gly Pro Val Ile Ile Asp Val Pro
530                 535                 540 gtt gac tac agt gat aac att aat tta gca agt gac aag ctt ccg aaa      1680
Val Asp Tyr Ser Asp Asn Ile Asn Leu Ala Ser Asp Lys Leu Pro Lys
545                 550                 555                 560 gaa ttc ggg gaa ctc atg aaa acg aaa gct ctc tag                      1716
Glu Phe Gly Glu Leu Met Lys Thr Lys Ala Leu
                565                 570

<210> SEQ ID NO 6
<211> LENGTH: 571
<212> TYPE: PRT
<213> ORGANISM: Artificial sequence
<220> FEATURE:
<223> OTHER INFORMATION: Synthetic Construct

<400> SEQUENCE: 6

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110
```

```
Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
        130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Asn Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525
```

```
Leu Arg Gln Gly Met Asn Ala Glu Gly Pro Val Ile Ile Asp Val Pro
            530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 7
<211> LENGTH: 571
<212> TYPE: PRT
<213> ORGANISM: Artificial sequence
<220> FEATURE:
<223> OTHER INFORMATION: Synthetic

<400> SEQUENCE: 7

Val Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320
```

```
Pro Asp Leu Glu Leu Ile Gly Asp Ile Pro Ser Thr Ile Asn His Ile
            325                 330                 335

Glu His Asp Ala Lys Val Glu Phe Ala Glu Arg Glu Gln Lys Ile
        340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
        370                 375                 380

Arg Asn Ala Val Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
            450                 455                 460

Val Arg Leu Lys Ala Pro Ile Val His Ile Val Trp Asn Asp Ser Thr
465                 470                 475                 480

Tyr Asp Met Val Ala Phe Asn Gln Leu Lys Lys Tyr Asn Arg Thr Ser
            485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570

<210> SEQ ID NO 8
<211> LENGTH: 1716
<212> TYPE: DNA
<213> ORGANISM: Artificial sequence
<220> FEATURE:
<223> OTHER INFORMATION: Synthetic
<220> FEATURE:
<221> NAME/KEY: CDS
<222> LOCATION: (1)..(1716)

<400> SEQUENCE: 8 atg ttg aca aaa gca aca aaa gaa caa aaa tcc ctt gtg aaa aac aga      48
Met Leu Thr Lys Ala Thr Lys Glu Gln Lys Ser Leu Val Lys Asn Arg
1               5                   10                  15 ggg gcg gag ctt gtt gtt gat tgc tta gtg gag caa ggt gtc aca cat      96
Gly Ala Glu Leu Val Val Asp Cys Leu Val Glu Gln Gly Val Thr His
            20                  25                  30 gta ttt ggc att cca ggt gca aaa att gat gcg gta ttt gac gct tta     144
Val Phe Gly Ile Pro Gly Ala Lys Ile Asp Ala Val Phe Asp Ala Leu
        35                  40                  45 caa gat aaa gga cct gaa att atc gtt gcc cgg cac gaa caa aac gca     192
Gln Asp Lys Gly Pro Glu Ile Ile Val Ala Arg His Glu Gln Asn Ala
    50                  55                  60
```

```
gca ttc atg gcc caa gca gtc ggc cgt tta act gga aaa ccg gga gtc     240
Ala Phe Met Ala Gln Ala Val Gly Arg Leu Thr Gly Lys Pro Gly Val
 65              70                  75                  80 gtg tta gtc aca tca gga ccg ggt gcc tct aac ttg gca aca ggc ctg     288
Val Leu Val Thr Ser Gly Pro Gly Ala Ser Asn Leu Ala Thr Gly Leu
                 85                  90                  95 ctg aca gcg aac act gaa gga gac cct gtc gtt gcg ctt gct gga aac     336
Leu Thr Ala Asn Thr Glu Gly Asp Pro Val Val Ala Leu Ala Gly Asn
                100                 105                 110 gtg atc cgt gca gat cgt tta aaa cgg aca cat caa tct ttg gat aat     384
Val Ile Arg Ala Asp Arg Leu Lys Arg Thr His Gln Ser Leu Asp Asn
            115                 120                 125 gcg gcg cta ttc cag ccg att aca aaa tac agt gta gaa gtt caa gat     432
Ala Ala Leu Phe Gln Pro Ile Thr Lys Tyr Ser Val Glu Val Gln Asp
        130                 135                 140 gta aaa aat ata ccg gaa gct gtt aca aat gca ttt agg ata gcg tca     480
Val Lys Asn Ile Pro Glu Ala Val Thr Asn Ala Phe Arg Ile Ala Ser
145                 150                 155                 160 gca ggg cag gct ggg gcc gct ttt gtg agc ttt ccg caa gat gtt gtg     528
Ala Gly Gln Ala Gly Ala Ala Phe Val Ser Phe Pro Gln Asp Val Val
                165                 170                 175 aat gaa gtc aca aat acg aaa aac gtg cgt gct gtt gca gcg cca aaa     576
Asn Glu Val Thr Asn Thr Lys Asn Val Arg Ala Val Ala Ala Pro Lys
                180                 185                 190 ctc ggt cct gca gca gat gat gca atc agt gcg gcc ata gca aaa atc     624
Leu Gly Pro Ala Ala Asp Asp Ala Ile Ser Ala Ala Ile Ala Lys Ile
            195                 200                 205 caa aca gca aaa ctt cct gtc gtt ttg gtc ggc atg aaa ggc gga aga     672
Gln Thr Ala Lys Leu Pro Val Val Leu Val Gly Met Lys Gly Gly Arg
        210                 215                 220 ccg gaa gca att aaa gcg gtt cgc aag ctt ttg aaa aag gtt cag ctt     720
Pro Glu Ala Ile Lys Ala Val Arg Lys Leu Leu Lys Lys Val Gln Leu
225                 230                 235                 240 cca ttt gtt gaa aca tat caa gct gcc ggt acc ctt tct aga gat tta     768
Pro Phe Val Glu Thr Tyr Gln Ala Ala Gly Thr Leu Ser Arg Asp Leu
                245                 250                 255 gag gat caa tat ttt ggc cgt atc ggt ttg ttc cgc aac cag cct ggc     816
Glu Asp Gln Tyr Phe Gly Arg Ile Gly Leu Phe Arg Asn Gln Pro Gly
                260                 265                 270 gat tta ctg cta gag cag gca gat gtt gtt ctg acg atc ggc tat gac     864
Asp Leu Leu Leu Glu Gln Ala Asp Val Val Leu Thr Ile Gly Tyr Asp
            275                 280                 285 ccg att gaa tat gat ccg aaa ttc tgg aat atc aat gga gac cgg aca     912
Pro Ile Glu Tyr Asp Pro Lys Phe Trp Asn Ile Asn Gly Asp Arg Thr
        290                 295                 300 att atc cat tta gac gag att atc gct gac att gat cat gct tac cag     960
Ile Ile His Leu Asp Glu Ile Ile Ala Asp Ile Asp His Ala Tyr Gln
305                 310                 315                 320 cct gat ctt gaa ttg atc ggt gac att ccg tcc acg atc aat cat atc    1008
Pro Asp Leu Glu Leu Ile Gly Asp Ile Pro Ser Thr Ile Asn His Ile
                325                 330                 335 gaa cac gat gct gtg aaa gtg gaa ttt gca gag cgt gag cag aaa atc    1056
Glu His Asp Ala Val Lys Val Glu Phe Ala Glu Arg Glu Gln Lys Ile
                340                 345                 350 ctt tct gat tta aaa caa tat atg cat gaa ggt gag cag gtg cct gca    1104
Leu Ser Asp Leu Lys Gln Tyr Met His Glu Gly Glu Gln Val Pro Ala
            355                 360                 365 gat tgg aaa tca gac aga gcg cac cct ctt gaa atc gtt aaa gag ttg    1152
Asp Trp Lys Ser Asp Arg Ala His Pro Leu Glu Ile Val Lys Glu Leu
        370                 375                 380
```

| | | | | | | | | | | | | | | | | |
|---|---|---|---|---|---|---|---|---|---|---|---|---|---|---|---|---|
| cgt | aat | gca | gtc | gat | gat | cat | gtt | aca | gta | act | tgc | gat | atc | ggt | tcg | 1200 |
| Arg | Asn | Ala | Val | Asp | Asp | His | Val | Thr | Val | Thr | Cys | Asp | Ile | Gly | Ser | |
| 385 | | | | 390 | | | | 395 | | | | | 400 | | | |
| cac | gcc | att | tgg | atg | tca | cgt | tat | ttc | cgc | agc | tac | gag | ccg | tta | aca | 1248 |
| His | Ala | Ile | Trp | Met | Ser | Arg | Tyr | Phe | Arg | Ser | Tyr | Glu | Pro | Leu | Thr | |
| | | | | 405 | | | | | 410 | | | | | 415 | | |
| tta | atc | atc | agt | aac | ggt | atg | caa | aca | ctc | ggc | gtt | gcg | ctt | cct | tgg | 1296 |
| Leu | Met | Ile | Ser | Asn | Gly | Met | Gln | Thr | Leu | Gly | Val | Ala | Leu | Pro | Trp | |
| | | | 420 | | | | | 425 | | | | | 430 | | | |
| gca | atc | ggc | gct | tca | ttg | gtg | aaa | ccg | gga | gaa | aaa | gtg | gtt | tct | gtc | 1344 |
| Ala | Ile | Gly | Ala | Ser | Leu | Val | Lys | Pro | Gly | Glu | Lys | Val | Val | Ser | Val | |
| | | 435 | | | | | 440 | | | | | 445 | | | | |
| tct | ggt | gac | ggc | ggt | ttc | tta | ttc | tca | gca | atg | gaa | tta | gag | aca | gca | 1392 |
| Ser | Gly | Asp | Gly | Gly | Phe | Leu | Phe | Ser | Ala | Met | Glu | Leu | Glu | Thr | Ala | |
| | 450 | | | | | 455 | | | | | 460 | | | | | |
| gtt | cga | cta | aaa | gca | cca | att | gta | cac | att | gta | tgg | aac | gac | agc | aca | 1440 |
| Val | Arg | Leu | Lys | Ala | Pro | Ile | Val | His | Ile | Val | Trp | Asn | Asp | Ser | Thr | |
| 465 | | | | 470 | | | | 475 | | | | | 480 | | | |
| tat | gac | atg | gtt | gca | ttc | gcc | caa | ttg | aaa | aaa | tat | aac | cgt | aca | tct | 1488 |
| Tyr | Asp | Met | Val | Ala | Phe | Ala | Gln | Leu | Lys | Lys | Tyr | Asn | Arg | Thr | Ser | |
| | | | | 485 | | | | | 490 | | | | | 495 | | |
| gcg | gtc | gat | ttc | gga | aat | atc | gat | atc | gtg | aaa | tat | gcg | gaa | agc | ttc | 1536 |
| Ala | Val | Asp | Phe | Gly | Asn | Ile | Asp | Ile | Val | Lys | Tyr | Ala | Glu | Ser | Phe | |
| | | | 500 | | | | | 505 | | | | | 510 | | | |
| gga | gca | act | ggc | ttg | cgc | gta | gaa | tca | cca | gac | cag | ctg | gca | gat | gtt | 1584 |
| Gly | Ala | Thr | Gly | Leu | Arg | Val | Glu | Ser | Pro | Asp | Gln | Leu | Ala | Asp | Val | |
| | | | 515 | | | | | 520 | | | | | 525 | | | |
| ctg | cgt | caa | ggc | atg | aac | gct | gaa | ggt | cct | gtc | atc | atc | gat | gtc | ccg | 1632 |
| Leu | Arg | Gln | Gly | Met | Asn | Ala | Glu | Gly | Pro | Val | Ile | Ile | Asp | Val | Pro | |
| | 530 | | | | | 535 | | | | | 540 | | | | | |
| gtt | gac | tac | agt | gat | aac | att | aat | tta | gca | agt | gac | aag | ctt | ccg | aaa | 1680 |
| Val | Asp | Tyr | Ser | Asp | Asn | Ile | Asn | Leu | Ala | Ser | Asp | Lys | Leu | Pro | Lys | |
| 545 | | | | 550 | | | | 555 | | | | | 560 | | | |
| gaa | ttc | ggg | gaa | ctc | atg | aaa | acg | aaa | gct | ctc | tag | | | | | 1716 |
| Glu | Phe | Gly | Glu | Leu | Met | Lys | Thr | Lys | Ala | Leu | | | | | | |
| | | | | 565 | | | | 570 | | | | | | | | |

<210> SEQ ID NO 9
<211> LENGTH: 571
<212> TYPE: PRT
<213> ORGANISM: Artificial sequence
<220> FEATURE:
<223> OTHER INFORMATION: Synthetic Construct

<400> SEQUENCE: 9

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

```
Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
        130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Ala Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525
```

Leu Arg Gln Gly Met Asn Ala Glu Gly Pro Val Ile Ile Asp Val Pro
            530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 10
<211> LENGTH: 571
<212> TYPE: PRT
<213> ORGANISM: Artificial sequence
<220> FEATURE:
<223> OTHER INFORMATION: Synthetic

<400> SEQUENCE: 10

Val Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Lys Val Glu Phe Ala Glu Arg Glu Gln Lys Ile
        340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
        370                 375                 380

Arg Asn Ala Val Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
        450                 455                 460

Val Arg Leu Lys Ala Pro Ile Val His Ile Val Trp Asn Asp Ser Thr
465                 470                 475                 480

Tyr Asp Met Val Ala Phe Ala Gln Leu Lys Lys Tyr Asn Arg Thr Ser
            485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570

<210> SEQ ID NO 11
<211> LENGTH: 36
<212> TYPE: DNA
<213> ORGANISM: Artificial sequence
<220> FEATURE:
<223> OTHER INFORMATION: Synthetic

<400> SEQUENCE: 11
acgcagtcga cctagagagc tttcgttttc atgagt                    36

<210> SEQ ID NO 12
<211> LENGTH: 34
<212> TYPE: DNA
<213> ORGANISM: Artificial sequence
<220> FEATURE:
<223> OTHER INFORMATION: Synthetic

<400> SEQUENCE: 12
cgggatccgt tgacaaaagc aacaaaagaa caaa                      34

<210> SEQ ID NO 13
<211> LENGTH: 36
<212> TYPE: DNA
<213> ORGANISM: Artificial sequence
<220> FEATURE:
<223> OTHER INFORMATION: Synthetic

```
<400> SEQUENCE: 13
acgcagtcga cctagagagc tttcgttttc atgagt                                     36

<210> SEQ ID NO 14
<211> LENGTH: 32
<212> TYPE: DNA
<213> ORGANISM: Artificial sequence
<220> FEATURE:
<223> OTHER INFORMATION: Synthetic

<400> SEQUENCE: 14
aataagacgt ctaagaaacc attattatca tg                                         32

<210> SEQ ID NO 15
<211> LENGTH: 25
<212> TYPE: DNA
<213> ORGANISM: Artificial sequence
<220> FEATURE:
<223> OTHER INFORMATION: Synthetic

<400> SEQUENCE: 15
gaatgcaacc atgtcatatg tgctg                                                 25

<210> SEQ ID NO 16
<211> LENGTH: 60
<212> TYPE: DNA
<213> ORGANISM: Artificial sequence
<220> FEATURE:
<223> OTHER INFORMATION: Synthetic

<400> SEQUENCE: 16
atggaacgac agcacatatg acatggttgc attcaaccaa ttgaaaaaat ataaccgtac           60

<210> SEQ ID NO 17
<211> LENGTH: 60
<212> TYPE: DNA
<213> ORGANISM: Artificial sequence
<220> FEATURE:
<223> OTHER INFORMATION: Synthetic

<400> SEQUENCE: 17
atggaacgac agcacatatg acatggttgc attcgcccaa ttgaaaaaat ataaccgtac           60
```